(12) United States Patent
Nakazawa et al.

(10) Patent No.: US 11,122,996 B2
(45) Date of Patent: Sep. 21, 2021

(54) BLOOD GLUCOSE MEASUREMENT DEVICE, BLOOD GLUCOSE CALCULATION METHOD, AND BLOOD GLUCOSE CALCULATION PROGRAM

(71) Applicant: HAMAMATSU PHOTONICS K.K., Hamamatsu (JP)

(72) Inventors: Tomoya Nakazawa, Hamamatsu (JP); Rui Sekine, Hamamatsu (JP); Masato Kitabayashi, Hamamatsu (JP); Anna Ienaka, Hamamatsu (JP); Yu Hashimoto, Hamamatsu (JP)

(73) Assignee: HAMAMATSU PHOTONICS K.K., Hamamatsu (JP)

( * ) Notice: Subject to any disclaimer, the term of this patent is extended or adjusted under 35 U.S.C. 154(b) by 225 days.

(21) Appl. No.: 16/338,550

(22) PCT Filed: Sep. 19, 2017

(86) PCT No.: PCT/JP2017/033685
§ 371 (c)(1),
(2) Date: Apr. 1, 2019

(87) PCT Pub. No.: WO2018/066350
PCT Pub. Date: Apr. 12, 2018

(65) Prior Publication Data
US 2020/0178858 A1    Jun. 11, 2020

(30) Foreign Application Priority Data
Oct. 3, 2016 (JP) ............................. JP2016-195948

(51) Int. Cl.
*A61B 5/145* (2006.01)
*A61B 5/1455* (2006.01)
*A61B 5/00* (2006.01)

(52) U.S. Cl.
CPC ...... *A61B 5/14532* (2013.01); *A61B 5/14551* (2013.01); *A61B 5/7239* (2013.01)

(58) Field of Classification Search
CPC ............ A61B 5/14532; A61B 5/14551; A61B 5/7239
(Continued)

(56) References Cited

U.S. PATENT DOCUMENTS 6,615,064 B1 * 9/2003 Aldrich .............. A61B 5/14532
600/316
2011/0230744 A1    9/2011 Ribas Ripoll et al.

FOREIGN PATENT DOCUMENTS

CN    104146714 A    11/2014
CN    105748059 A    7/2016
(Continued)

OTHER PUBLICATIONS

International Preliminary Report on Patentability dated Apr. 18, 2019 for PCT/JP2017/033685.

*Primary Examiner* — Erin M Piateski
(74) *Attorney, Agent, or Firm* — Faegre Drinker Biddle & Reath LLP

(57) ABSTRACT

A blood glucose measurement device, a blood glucose calculation method, and a blood glucose calculation program capable of accurately measuring a blood glucose level by using light are provided. The blood glucose measurement device includes a light source 11 that outputs measurement light L1 to be input to a living body 50; a light detector 12 that detects the measurement light L1 propagated inside the living body 50 and generates a detection signal in accordance with an intensity of the measurement light L1; and a computation unit that obtains a time lag between a temporal change in a first parameter related to an oxygenated hemoglobin concentration and a temporal change in a second parameter related to a deoxygenated hemoglobin concentra-
(Continued)

tion based on the detection signal, and obtains the data related to the blood glucose level based on the time lag.

22 Claims, 16 Drawing Sheets

(58) Field of Classification Search
USPC .......................................................... 600/301
See application file for complete search history.

(56) References Cited

FOREIGN PATENT DOCUMENTS

| | | |
|---|---|---|
| DE | 202006016176 U1 | 1/2007 |
| JP | H10-325794 A | 12/1998 |
| JP | 2004-329542 A | 11/2004 |
| JP | 2005-253478 A | 9/2005 |
| JP | 2007-151618 A | 6/2007 |
| JP | 2009-520548 A | 5/2009 |
| JP | 2009-535072 A | 10/2009 |
| JP | 2011-24698 A | 2/2011 |
| JP | 2013-169470 A | 9/2013 |
| KR | 101512076 B1 | 4/2015 |
| WO | WO-2007/072300 A2 | 6/2007 |
| WO | WO-2007/122557 A2 | 11/2007 |
| WO | WO-2015/130333 A1 | 9/2015 |

\* cited by examiner (a)

(b)

(a)

(b)

(c)

(a)

(b)

(a)

(b)

(a)

(b)

(a)

(b)

BLOOD GLUCOSE MEASUREMENT DEVICE, BLOOD GLUCOSE CALCULATION METHOD, AND BLOOD GLUCOSE CALCULATION PROGRAM

CROSS-REFERENCE TO RELATED APPLICATIONS

This application is a National Stage Entry of International Application No. PCT/JP2017/033685, filed Sep. 19, 2017, which claims the benefit of Japanese Patent Application No. 2016-195948, filed Oct. 3, 2016, the contents of each of which is incorporated herein by reference.

TECHNICAL FIELD

The present disclosure relates a blood glucose measurement device, a blood glucose calculation method, and a blood glucose calculation program.

BACKGROUND ART

As devices for measuring a blood glucose level inside a living body in a non-invasive manner, for example, there are devices as disclosed in Patent Literature 1 and Patent Literature 2. The device disclosed in Patent Literature 1 obtains a glucose concentration by irradiating the inside of a living body with near-infrared light within a range of 1,480 nm to 1,880 nm, and detecting the near-infrared light propagated through the living body. In order to reduce the influence of light absorption due to components other than glucose, this device quantitatively obtains a glucose concentration by using an absorption signal having a wavelength region of 1,550 nm to 1,650 nm for measuring absorption derived from the OH groups of glucose molecules, an absorption signal having a wavelength region of 1,480 nm to 1,550 nm for measuring absorption derived from the NH groups of components of a living body, and an absorption signal having a wavelength region of 1,650 nm to 1,880 nm for measuring absorption derived from the CH groups of components of the living body, and by performing multi-variable analysis of these three absorption signals.

The device disclosed in Patent Literature 2 utilizes heat dissipation in glycometabolism. That is, the device disclosed in Patent Literature 2 obtains a blood glucose level based on a plurality of body-surface temperatures measured with a temperature sensor, and a parameter corresponding to the oxygen content of blood measured with a near-infrared spectroscopy (NIRS) sensor.

CITATION LIST

Patent Literature

Patent Literature 1: Japanese Unexamined Patent Publication No. H10-325794
Patent Literature 2: Japanese Unexamined Patent Publication No. 2004-329542

SUMMARY OF INVENTION

Technical Problem

Generally, diabetes is a disease with which there is unlikely to be awareness thereof. Therefore, it is necessary to regularly take a medical examination, such as a blood examination, for early detection. Diabetes is an illness with which the blood glucose level rises excessively due to the deterioration of insulin action. As a method of measuring a blood glucose level inside a living body, for example, there is a method of collecting blood by pricking the skin of an examinee with a puncture needle, but such a method causes an examinee to suffer pain. Therefore, the inventor has conceived establishment of a non-invasive measuring technique in which the blood glucose level is measured without collecting blood. As a non-invasive measuring technique of measuring a blood glucose level, a method of measuring a blood glucose level by using light can be conceived. For example, a device disclosed in Patent Literature 1 utilizes near-infrared light absorbed by glucose. However, a part of an absorption wavelength region of glucose overlaps the absorption wavelength regions of components such as water, lipids, and proteins. For example, the concentrations of these components change due to a meal or the like at any time. Therefore, in a method of utilizing light absorption of glucose, these components may adversely affect the measurement accuracy as noise. Consequently, there is concern that the measurement accuracy of a blood glucose level will be degraded. In a device disclosed in Patent Literature 2, the error increases when the heat of glycometabolism is small, such that it is difficult to obtain an accurate blood glucose level.

An object of an embodiment is to provide a blood glucose measurement device, a blood glucose calculation method, and a blood glucose calculation program capable of accurately measuring a blood glucose level by using light.

Solution to Problem

According to an embodiment of the present invention, there is provided a blood glucose measurement device. The blood glucose measurement device includes a light outputting unit configured to output measurement light to be input to a living body; a light detecting unit configured to detect the measurement light propagated inside the living body and generate a detection signal in accordance with an intensity of the measurement light; and a computation unit configured to obtain a time lag between a temporal change in a first parameter related to an oxygenated hemoglobin concentration and a temporal change in a second parameter related to a deoxygenated hemoglobin concentration based on the detection signal, and obtain the data related to the blood glucose level based on the time lag.

In addition, according to another embodiment of the present invention, there is provided a blood glucose calculation method. The blood glucose calculation method includes a first computation step of obtaining a time lag between a temporal change in a first parameter related to an oxygenated hemoglobin concentration and a temporal change in a second parameter related to a deoxygenated hemoglobin concentration in the living body, and a second computation step of obtaining the data related to the blood glucose level based on the time lag.

In addition, according to another embodiment of the present invention, there is provided a blood glucose calculation program. The blood glucose calculation program causes a computer to execute a first computation step of obtaining a time lag between a temporal change in a first parameter related to an oxygenated hemoglobin concentration and a temporal change in a second parameter related to a deoxygenated hemoglobin concentration in the living body, and a second computation step of obtaining the blood glucose level based on the time lag.

Advantageous Effects of Invention

According to the blood glucose measurement device, the blood glucose calculation method, and the blood glucose calculation program of the embodiments, a blood glucose level can be accurately measured by using light.

Figure 3:
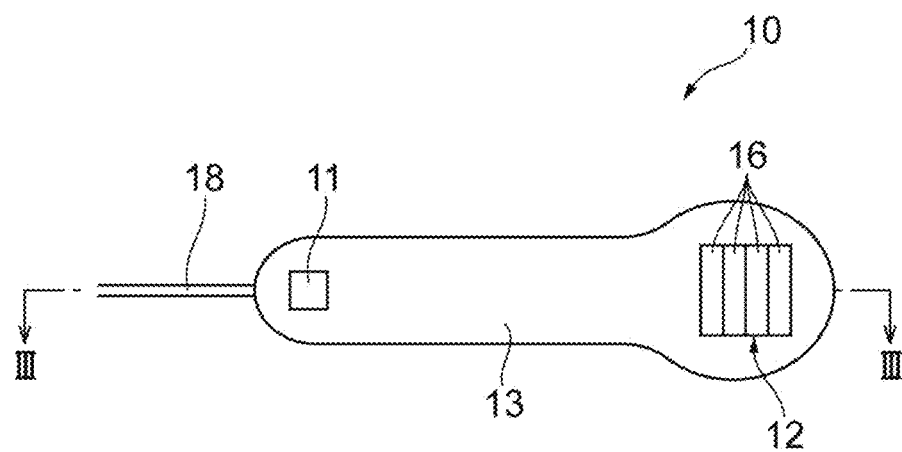
Figure 3:
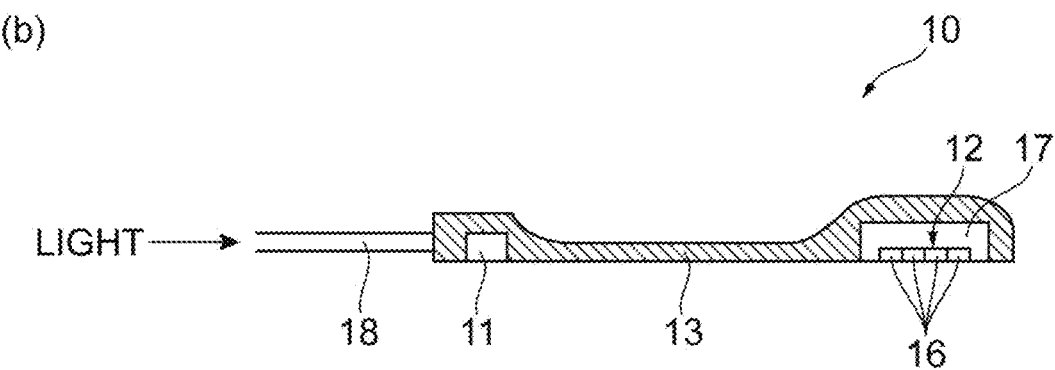

The part (a) of FIG. 3 is a plan view illustrating a configuration of the light measurement instrument, and the part (b) of FIG. 3 is a sectional side view cut along line in the part (a).

Figure 4:
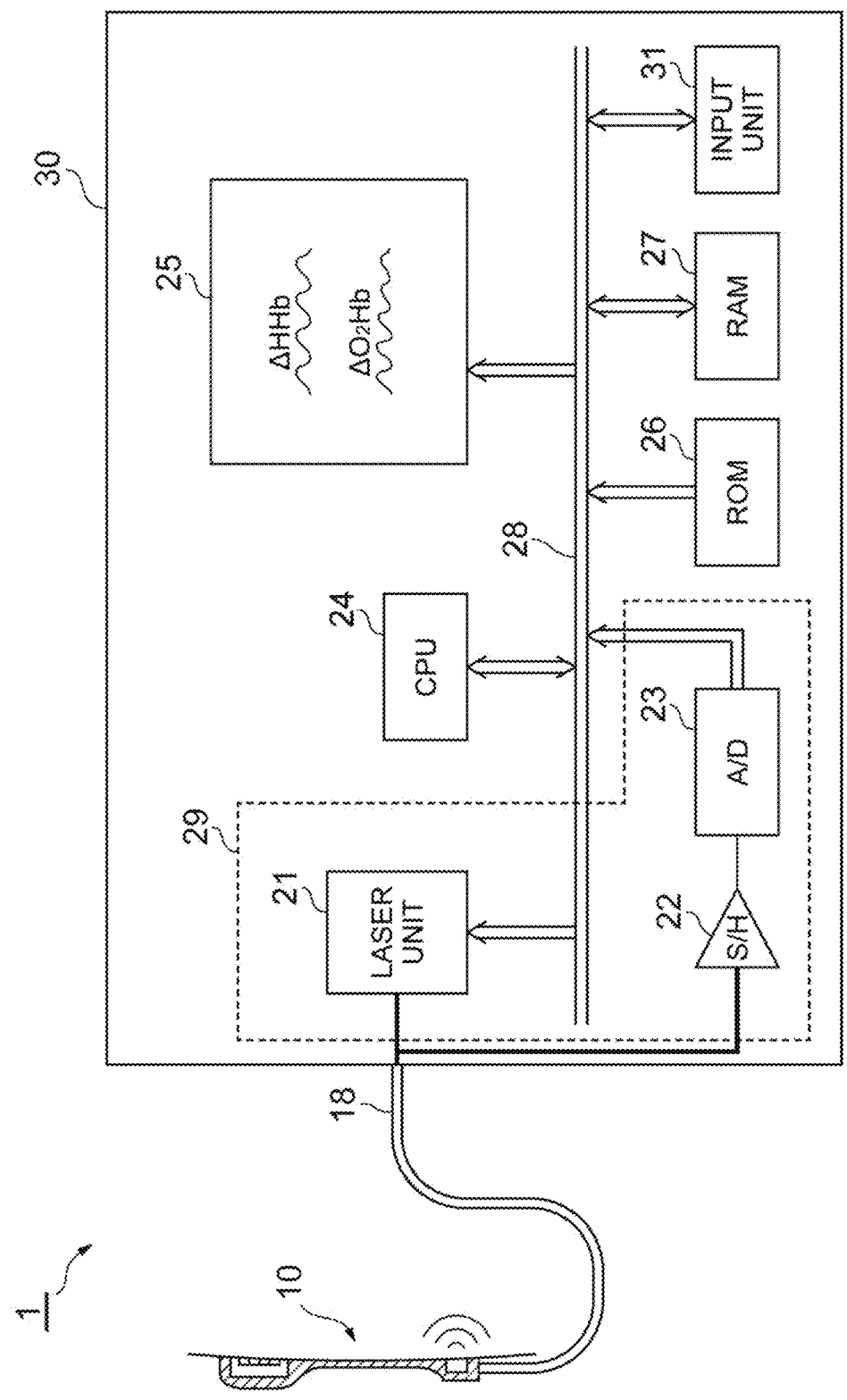

FIG. 4 is a block diagram illustrating an example of a configuration of the blood glucose measurement device.

Figure 5:
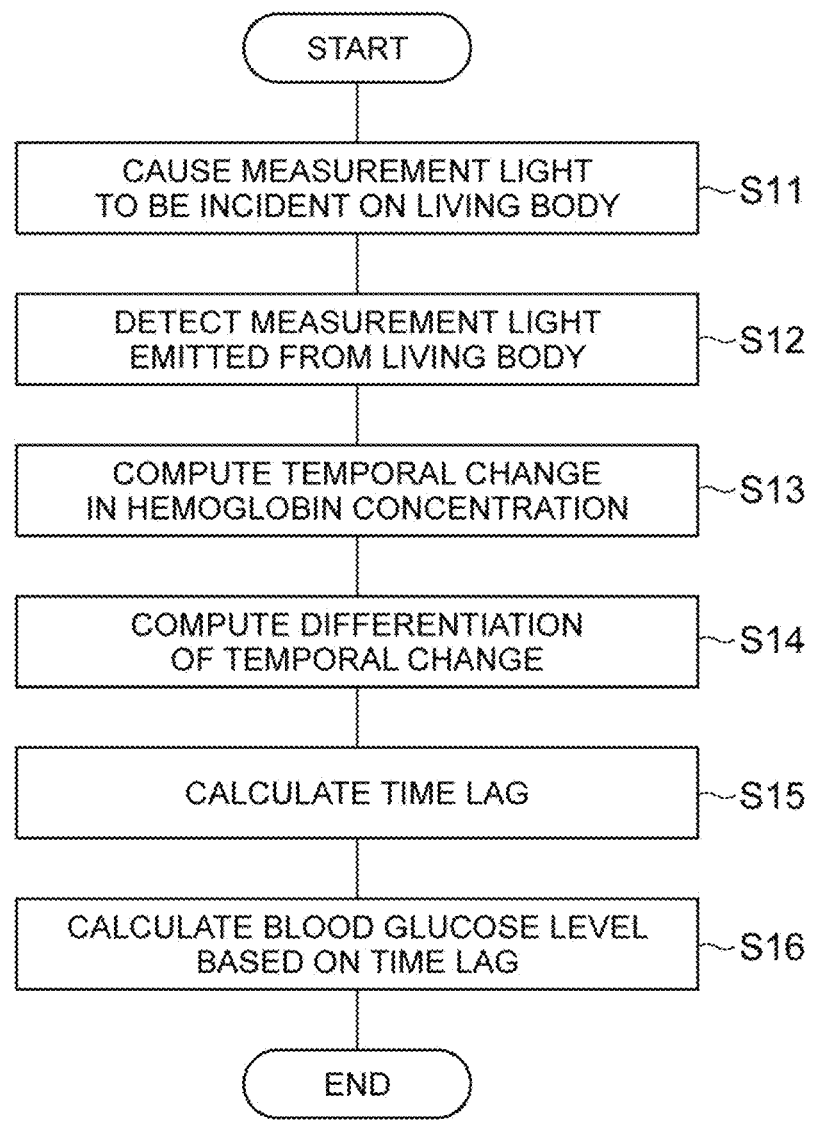

FIG. 5 is a flowchart illustrating a blood glucose calculation method according to another embodiment.

Figure 6:
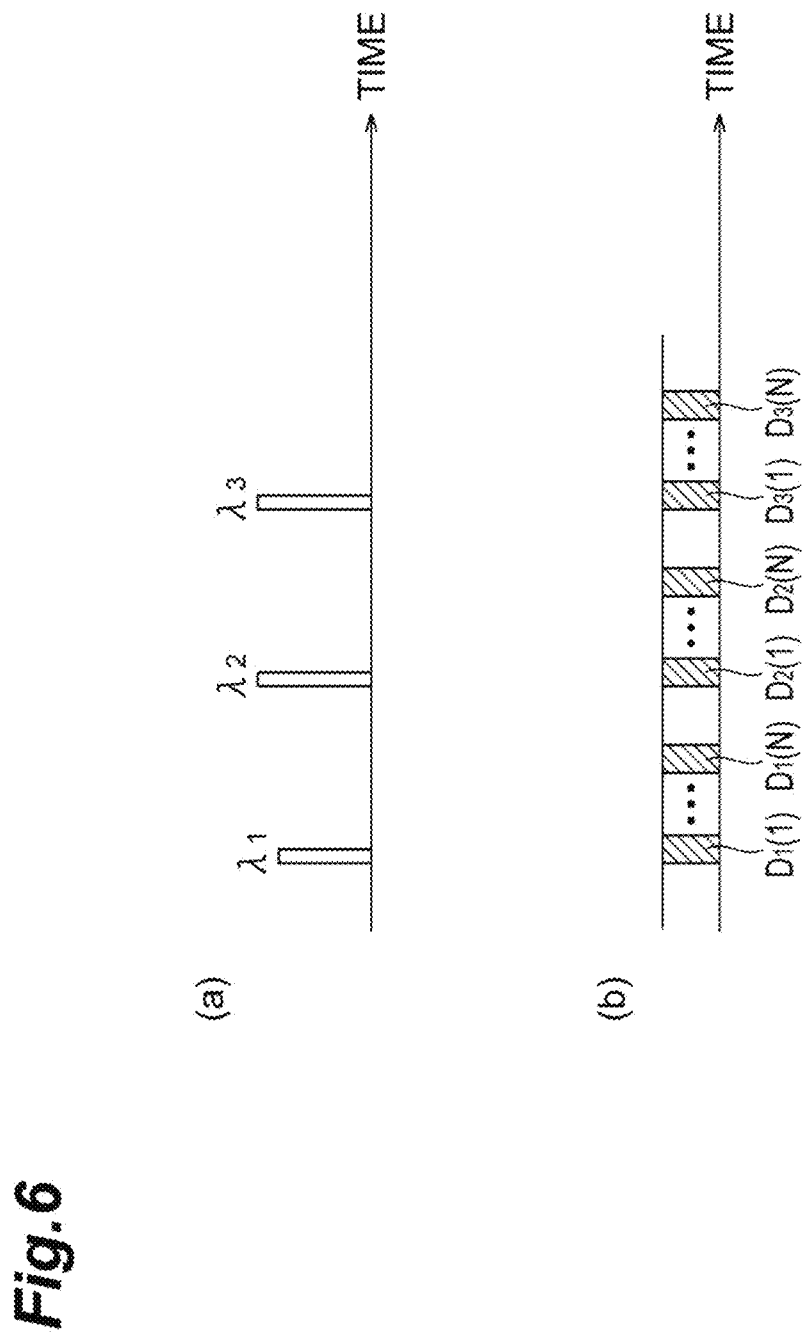

The part (a) of FIG. 6 is a view illustrating an input timing of laser beams having different wavelengths, and the part (b) of FIG. 6 is a view illustrating an output timing of a digital signal from an A/D converter circuit.

Figure 7:
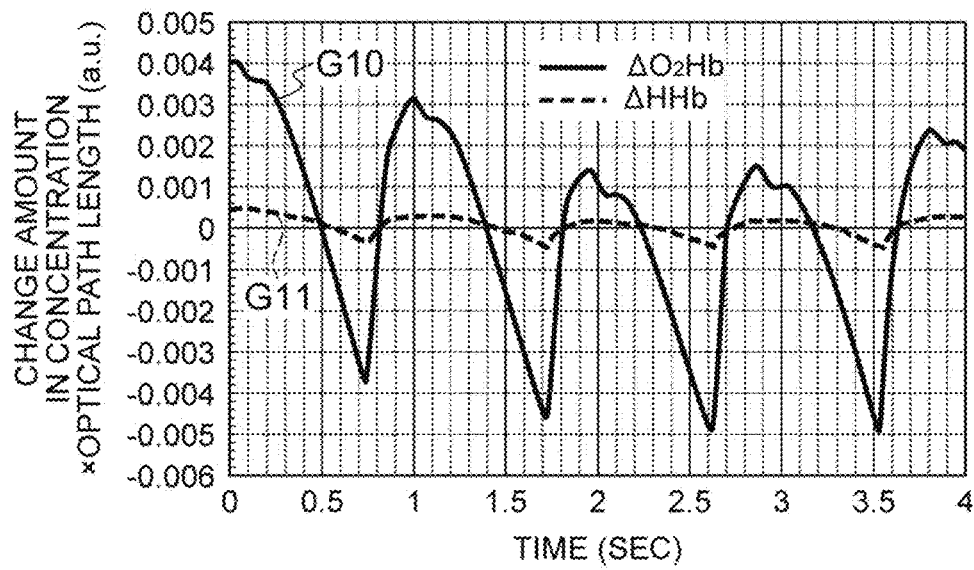
Figure 7:
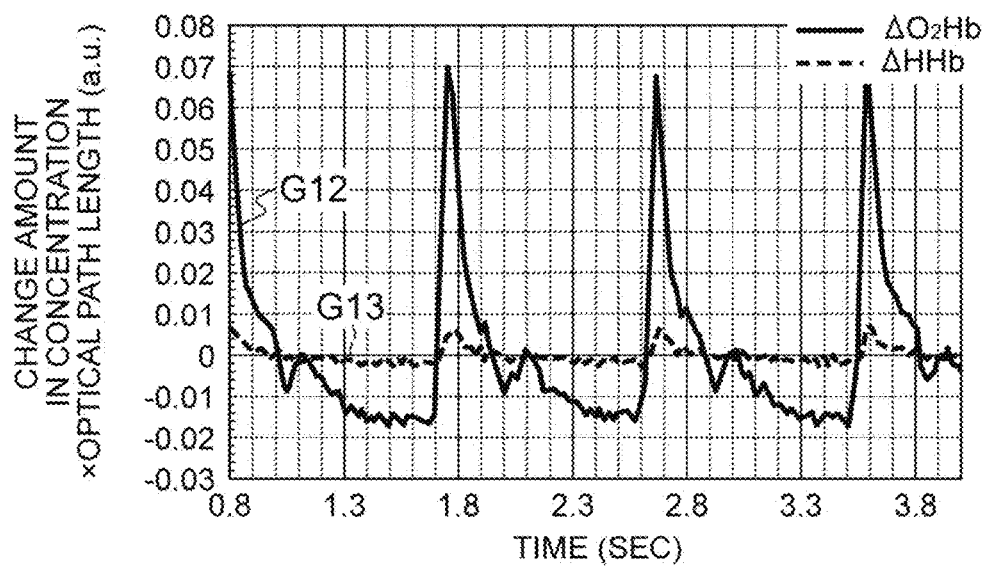
Figure 7:
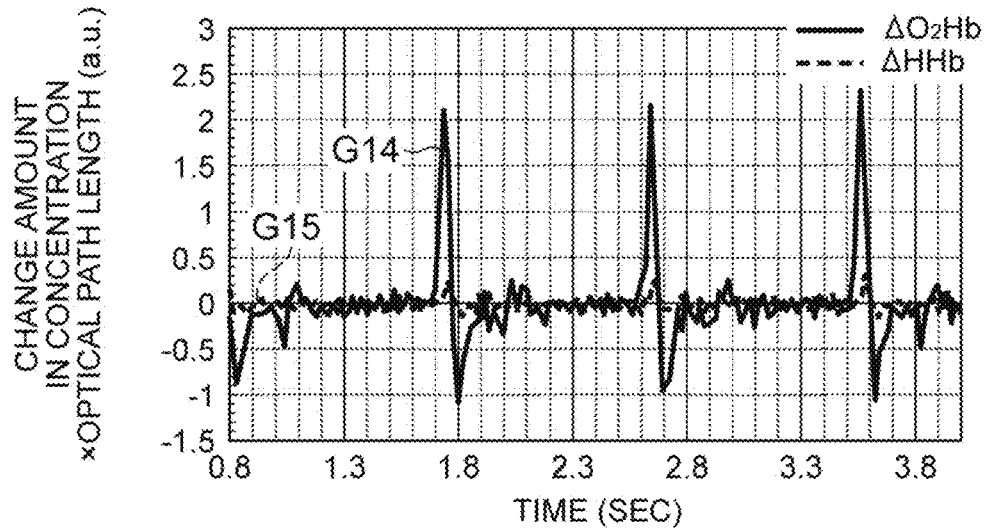

The part (a) of FIG. 7 is a graph showing time-series data of actual measurement values of each of $\Delta O_2Hb$ and $\Delta HHb$, the part (b) of FIG. 7 is a graph showing data obtained by performing differentiation of the time-series data of the actual measurement values of each of $\Delta O_2Hb$ and $\Delta HHb$ once, and the part (c) of FIG. 7 is a graph showing values obtained by performing differentiation of the time-series data of the actual measurement values of each of $\Delta O_2Hb$ and $\Delta HHb$ twice.

Figure 8:
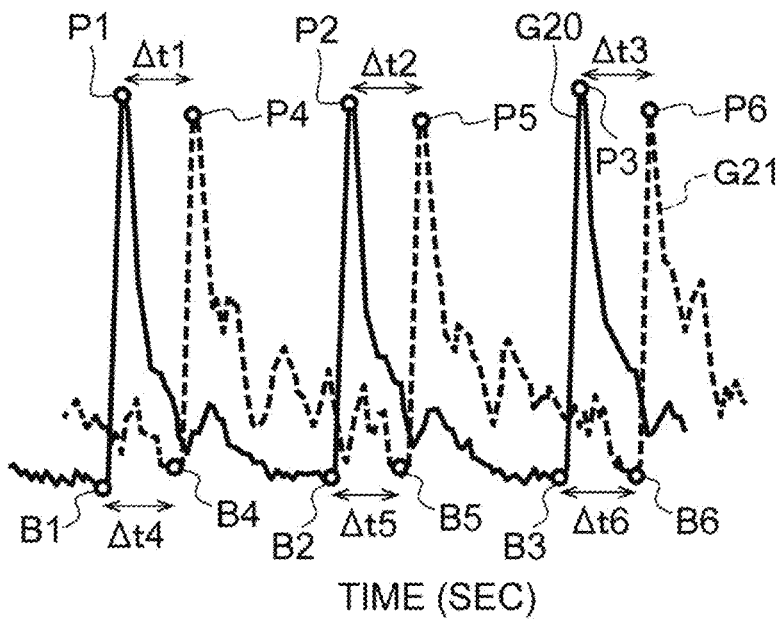
Figure 8:
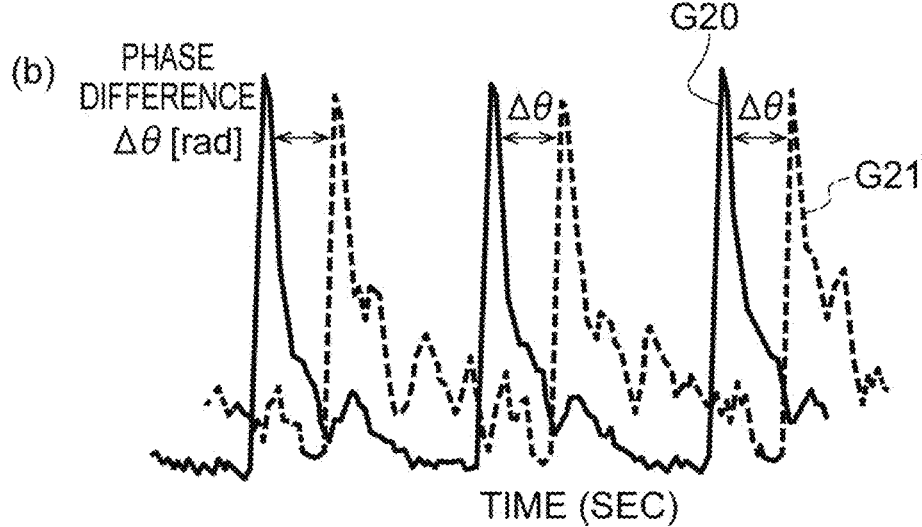
Figure 8:
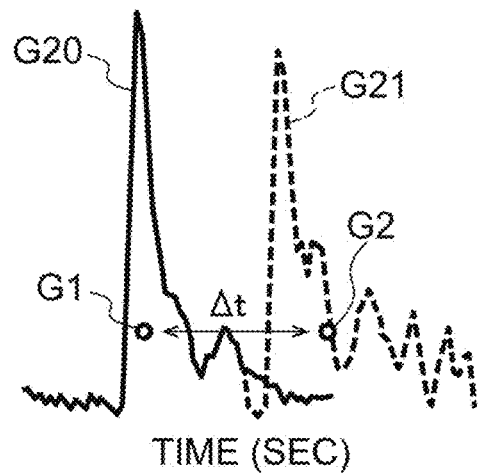

The part (a) of FIG. 8 is a graph for describing a method of calculating a time lag performed by extracting a feature point in the data obtained by performing differentiation of the time-series data of the actual measurement values of $\Delta O_2Hb$ and $\Delta HHb$ once, the part (b) of FIG. 8 is a graph for describing a method of calculating a time lag performed based on an inner product of functions of the data obtained by performing differentiation of the time-series data of the actual measurement values of $\Delta O_2Hb$ and $\Delta HHb$ once, and the part (c) of FIG. 8 is a graph for describing a method of calculating a time lag performed by extracting a centroid position in the data obtained by performing differentiation of the time-series data of the actual measurement values of $\Delta O_2Hb$ and $\Delta HHb$ once.

Figure 9:
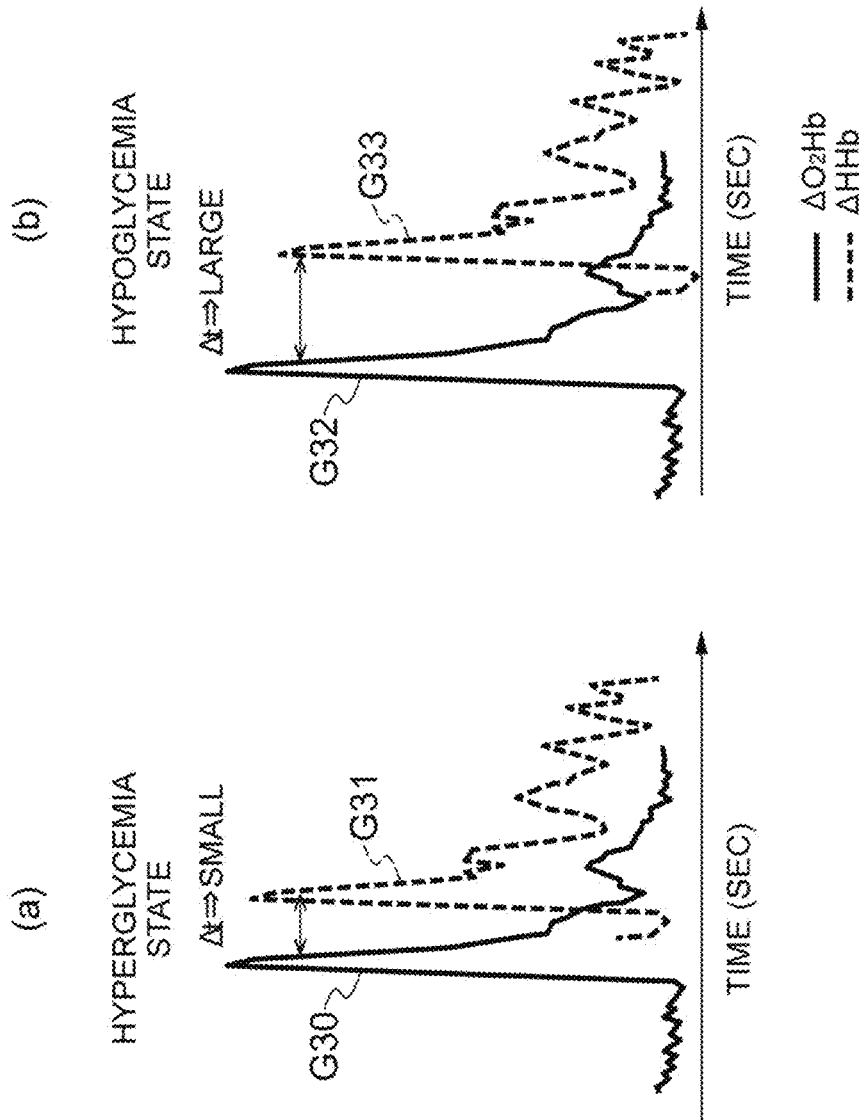

The part (a) of FIG. 9 is a graph showing the time-series data of the actual measurement values of $\Delta O_2Hb$ and $\Delta HHb$ when an examinee is in a hyperglycemia state, and the part (b) of FIG. 9 is a graph showing the time-series data of the actual measurement values of $\Delta O_2Hb$ and MEM when an examinee is in a hypoglycemia state.

Figure 10:
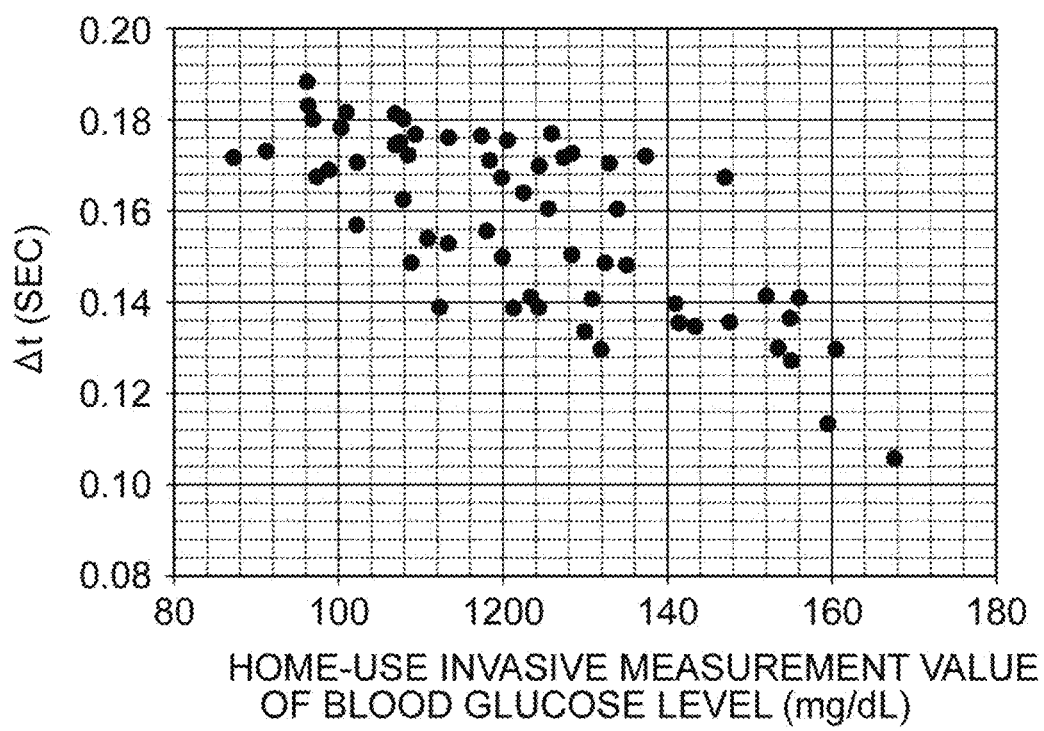

FIG. 10 is a scatter diagram showing a correlationship between a blood glucose level of an examinee obtained by using an invasive blood glucose meter and a time lag between $\Delta O_2Hb$ and $\Delta HHb$.

Figure 11:
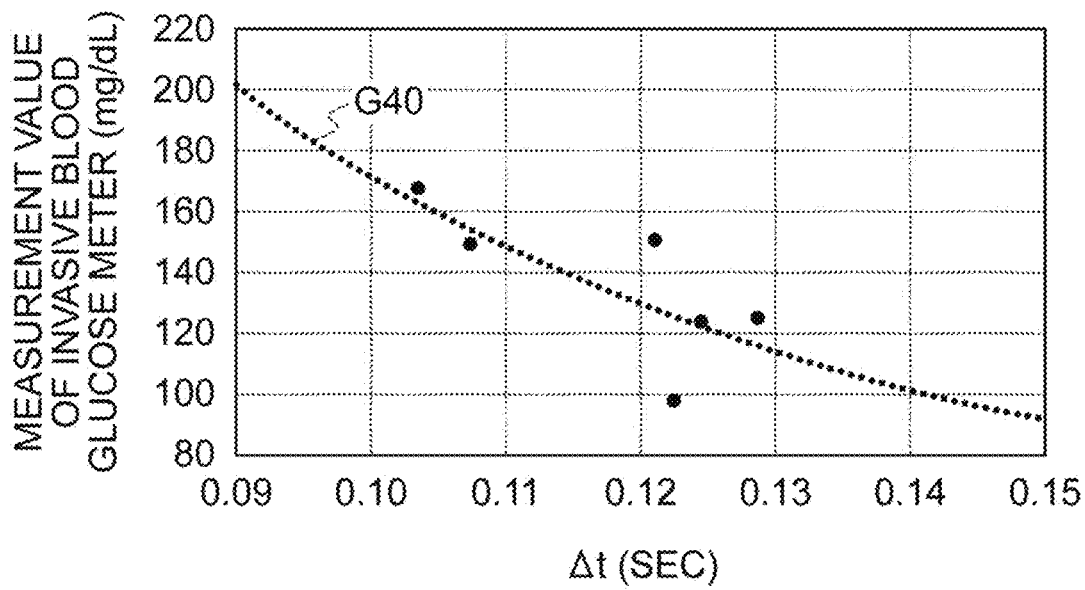
Figure 11:
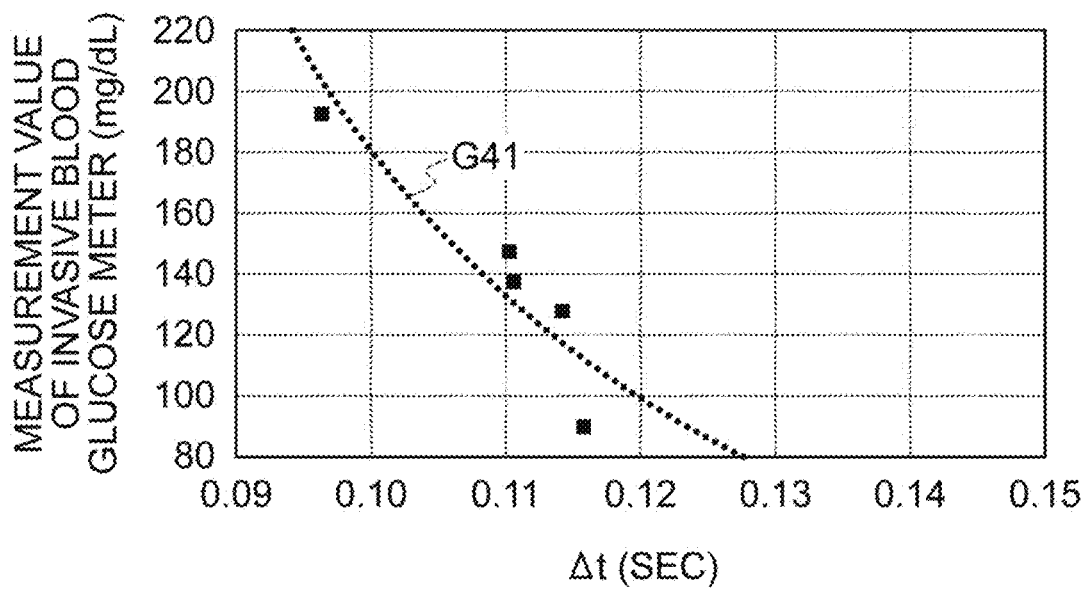

FIG. 11 is a scatter diagram showing a correlationship between a blood glucose level of an examinee obtained by using an invasive blood glucose meter and a time lag between $\Delta O_2Hb$ and $\Delta HHb$.

Figure 12:
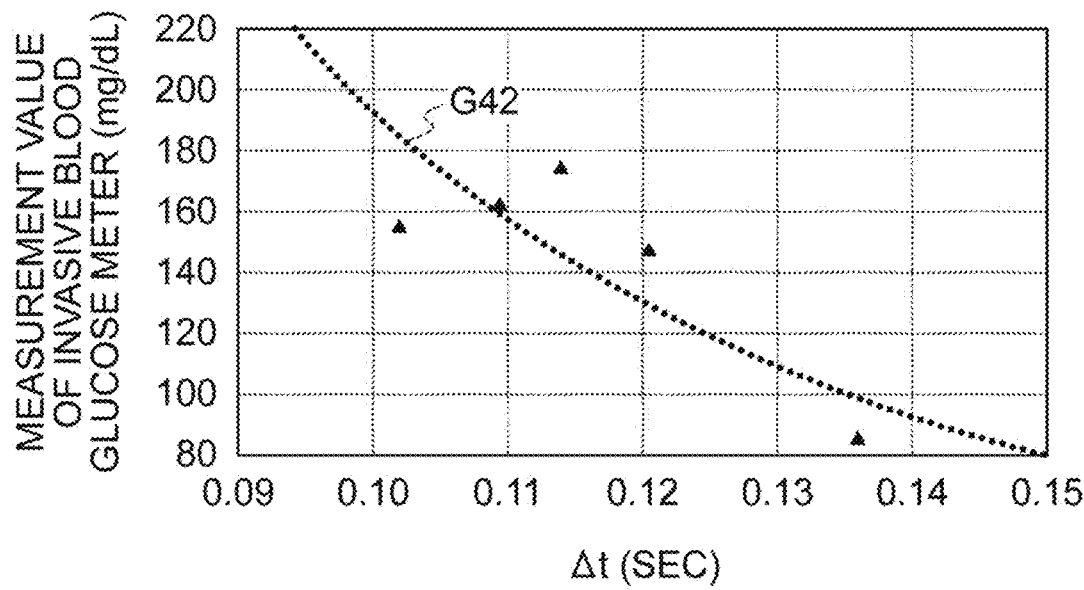
Figure 12:
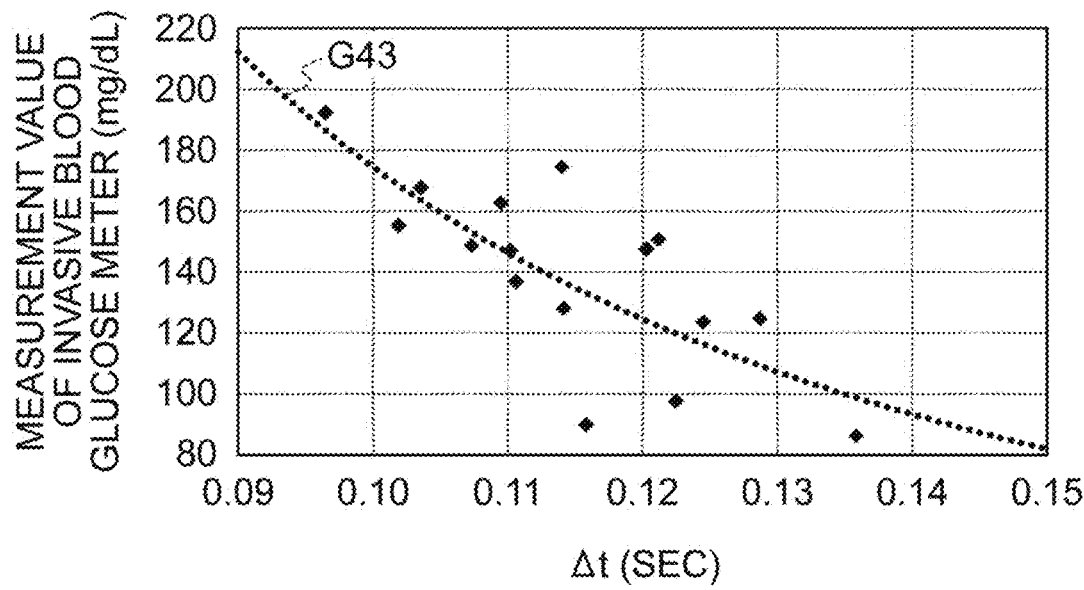

The part (a) of FIG. 12 is a scatter diagram showing a correlationship between a blood glucose level of an examinee obtained by using an invasive blood glucose meter and a time lag between $\Delta O_2Hb$ and $\Delta HHb$, and the part (b) of FIG. 12 is a view in which the scatter diagrams of the part (a) of FIG. 11, the part (b) of FIG. 11, and the part (a) of FIG. 12 are combined in one diagram.

Figure 13:
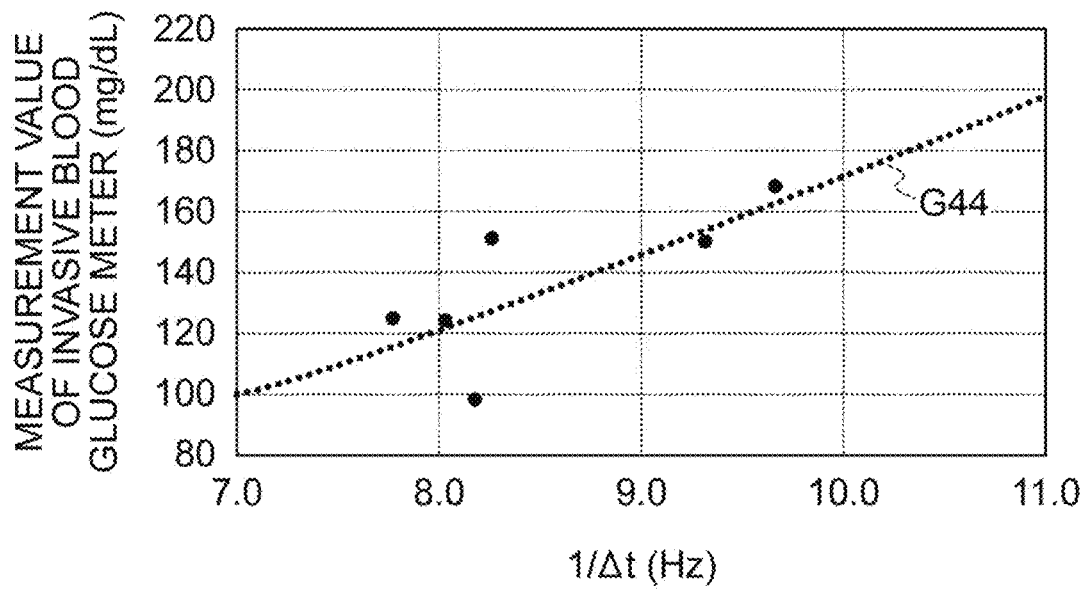
Figure 13:
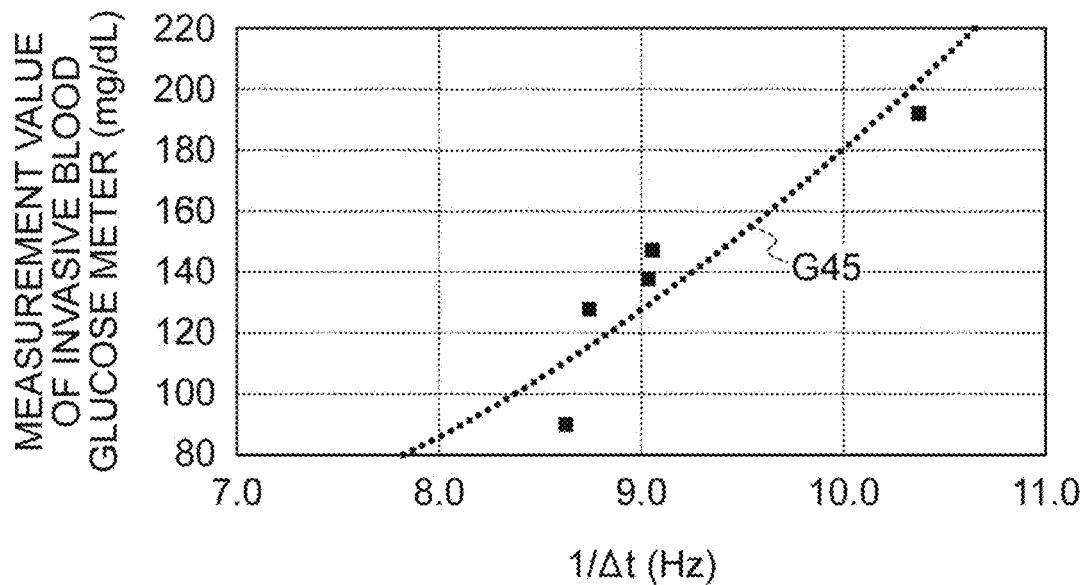

The part (a) of FIG. 13 is a scatter diagram when the horizontal axis in the part (a) of FIG. 11 is set to the reciprocal of the time lag, and the part (b) of FIG. 13 is a scatter diagram when the horizontal axis in the part (b) of FIG. 11 is set to the reciprocal of the time lag.

Figure 14:
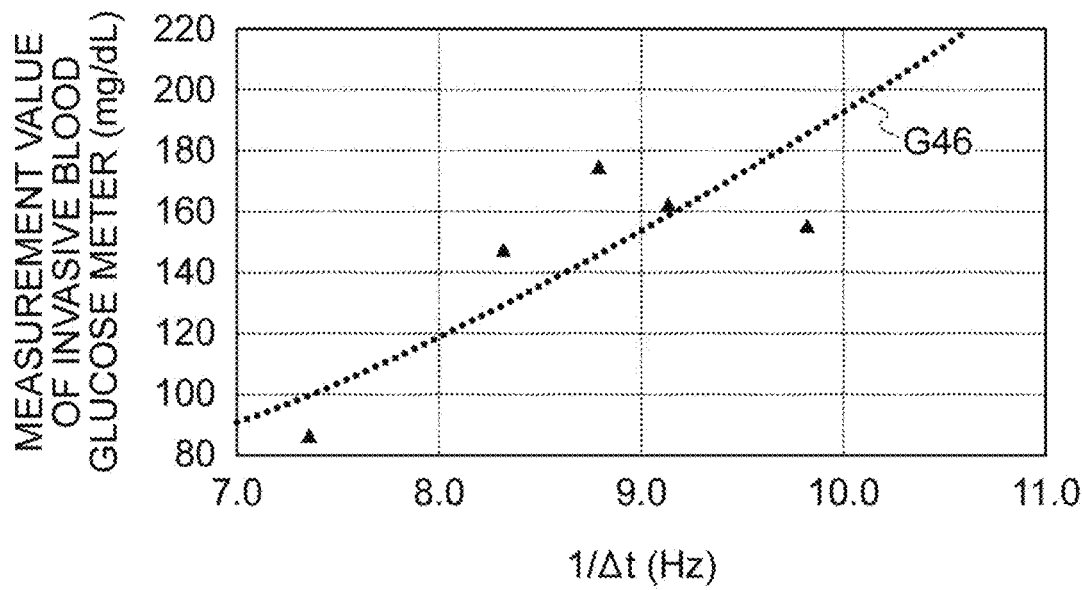
Figure 14:
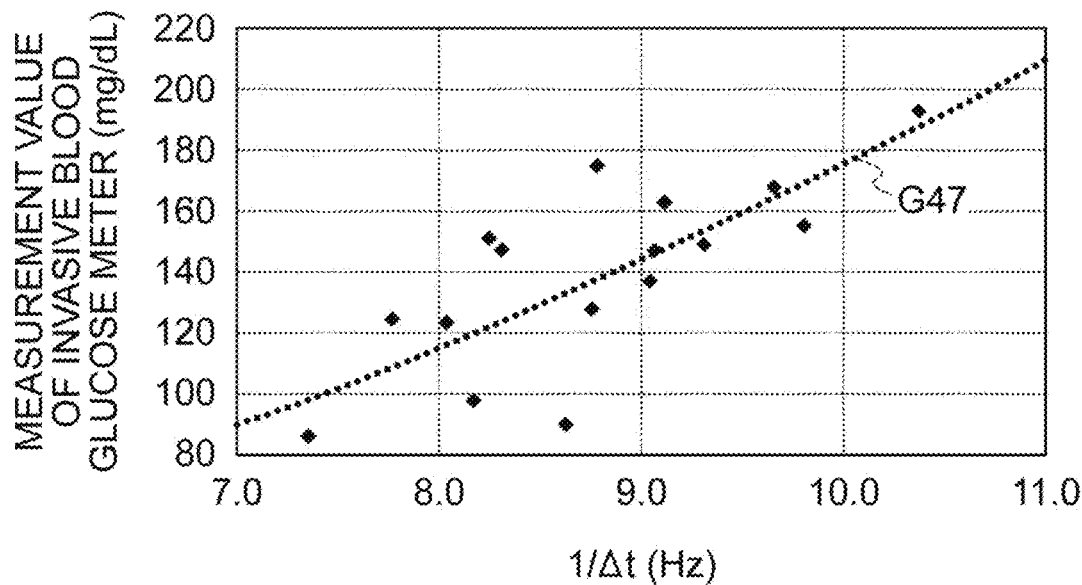

The part (a) of FIG. 14 is a scatter diagram when the horizontal axis in the part (a) of FIG. 12 is set to the reciprocal of the time lag, and the part (b) of FIG. 14 is a scatter diagram when the horizontal axis in the part (b) of FIG. 12 is set to the reciprocal of the time lag.

Figure 15:
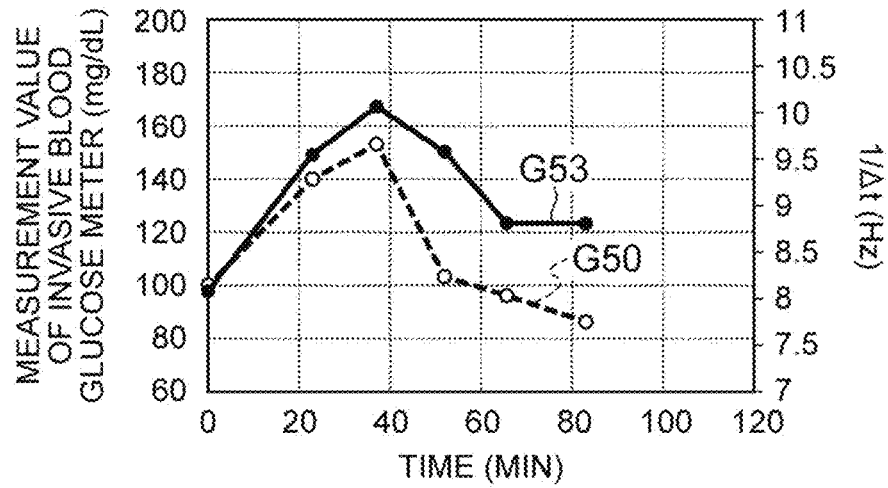
Figure 15:
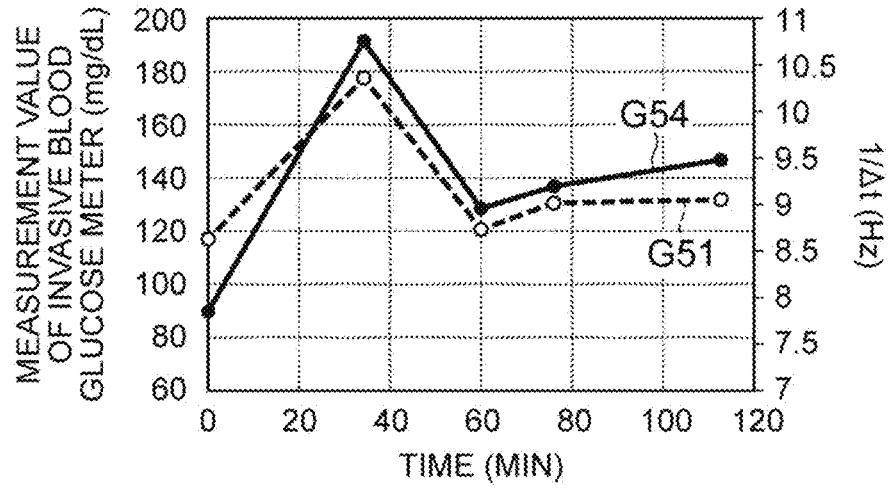
Figure 15:
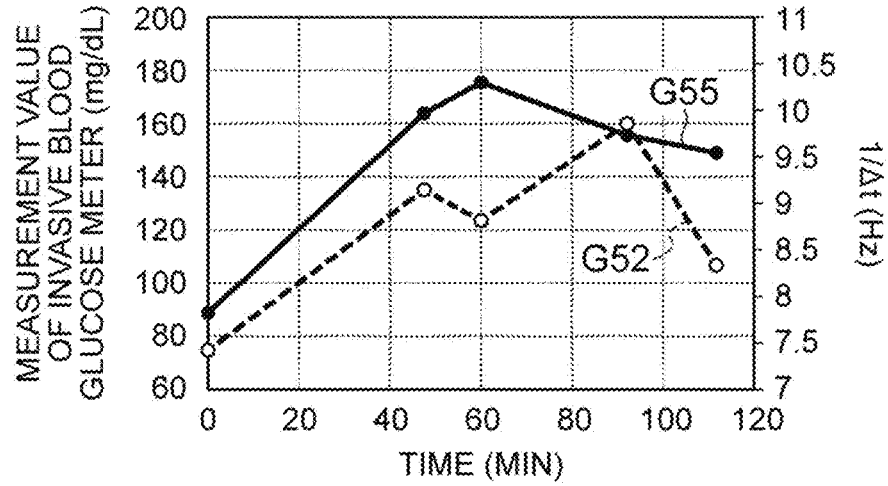

FIG. 15 is a graph collectively showing a time change in the blood glucose level of an examinee obtained by using an invasive blood glucose meter, and a time change in the reciprocal of the time lag between $\Delta O_2Hb$ and $\Delta HHb$.

Figure 16:
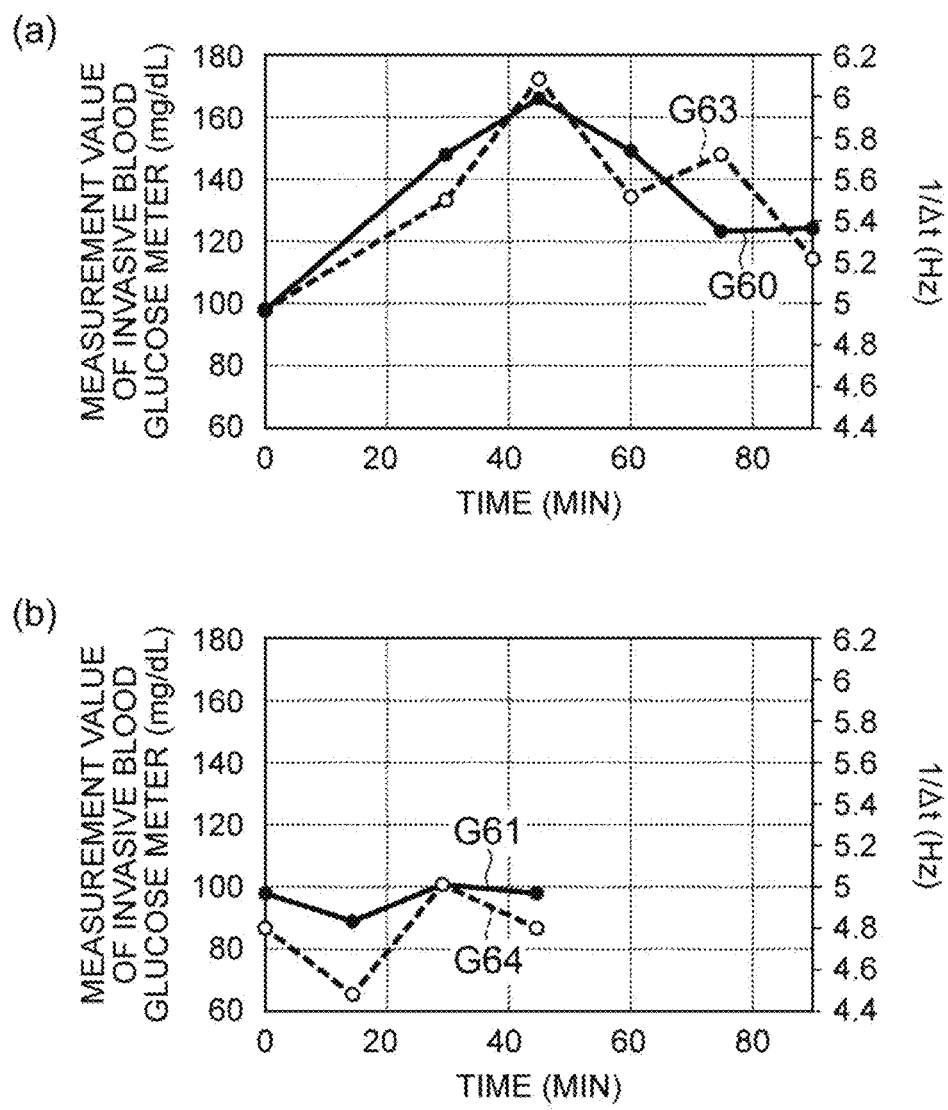

FIG. 16 is a graph collectively showing a time change in the blood glucose level of an examinee obtained by using an invasive blood glucose meter, and a time change in the reciprocal of the time lag between $\Delta O_2Hb$ and $\Delta HHb$.

DESCRIPTION OF EMBODIMENT

Figure 1:
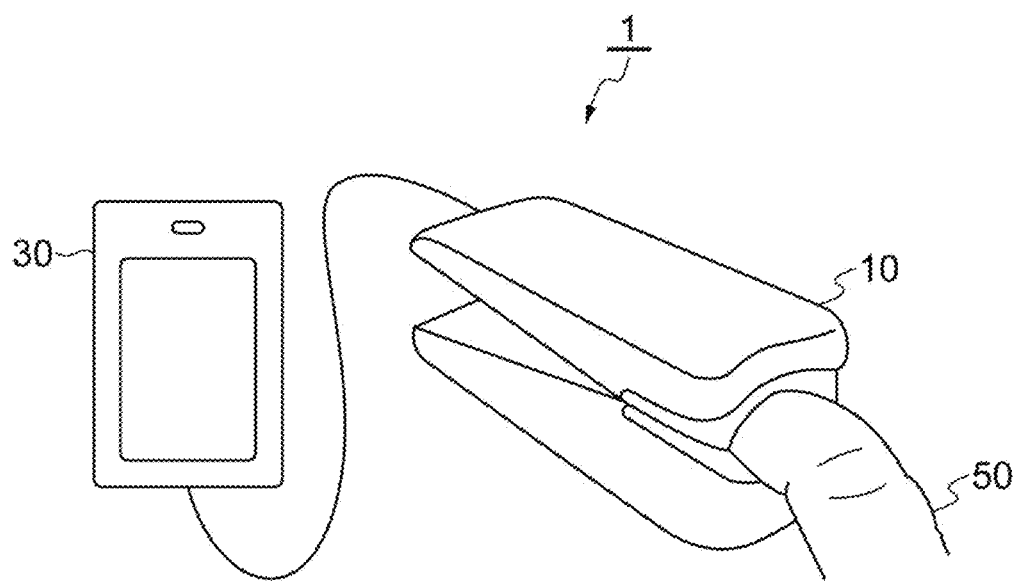
FIG. 1 is a conceptual diagram of a blood glucose measurement device according to an embodiment.

Hereinafter, embodiments of a blood glucose measurement device (blood glucose level calculation device), a blood glucose calculation method (blood glucose level measurement method), and a blood glucose calculation program (blood glucose level measurement program) will be described in detail with reference to the accompanying drawings. The same reference signs are applied to the same elements in description of the drawings, and duplicated description will be omitted. FIG. 1 is a conceptual diagram of a blood glucose measurement device 1 according to the present embodiment. The blood glucose measurement device 1 includes a light measurement instrument (probe) 10 and a main body unit 30. The main body unit 30 obtains a temporal change in a parameter (first parameter) related to an oxygenated hemoglobin ($O_2Hb$) concentration and a temporal change in a parameter (second parameter) related to a deoxygenated hemoglobin (HHb) concentration based on the intensity of light detected from a living body 50 by the light measurement instrument 10. For example, the parameter related to the $O_2Hb$ concentration is a temporal fluctuation from an initial amount (relative amount of temporal change ($\Delta O_2Hb$)) in the $O_2Hb$ concentration, an absolute value ($O_2Hb$) of the $O_2Hb$ concentration at a certain time, a time differential value of these $O_2Hb$ concentrations, or the like. In addition, the parameter related to the HHb concentration is a temporal fluctuation from an initial amount (relative amount of temporal change ($\Delta HHb$)) in the HHb concentration, an absolute value (HHb) of the HHb concentration at a certain time, a time differential value of these HHb concentrations, or the like. In addition, the temporal change in parameters related to the $O_2Hb$ concentration and the temporal change in parameters related to the HHb concentration are time-series data of these parameters, for example. The main body unit 30 calculates the blood glucose level based on a time lag therebetween and informs an examinee of the blood glucose level. For example, the main body unit 30 is constituted of a computer such as a personal computer, a microcomputer, a cloud server, or a smart device (a smartphone, a tablet terminal, or the like).

Figure 2:
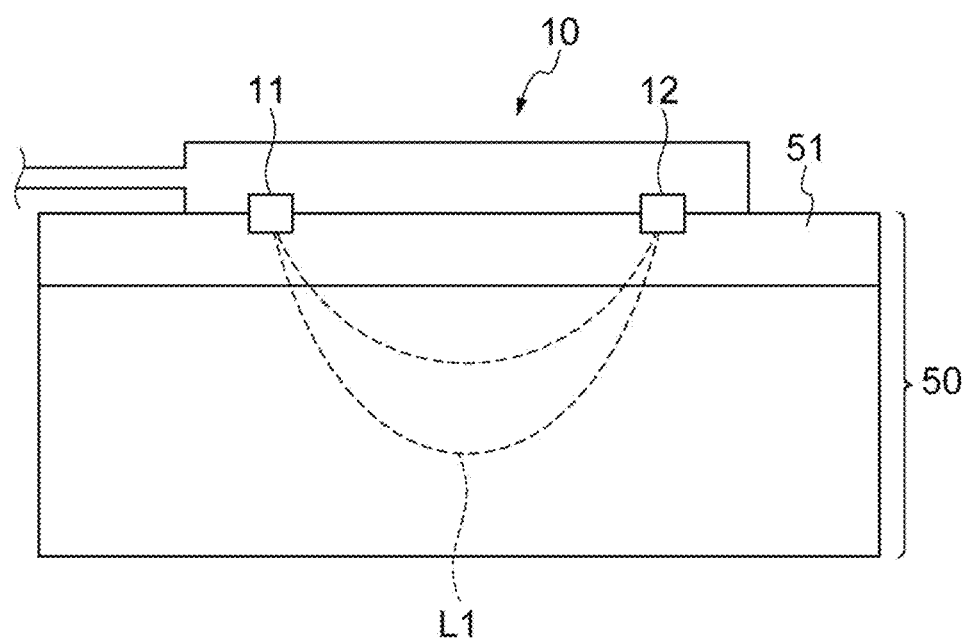
FIG. 2 is a conceptual diagram of a light measurement instrument according to the embodiment.

FIG. 2 is a conceptual diagram of the light measurement instrument 10 according to the present embodiment. The light measurement instrument 10 has a light source (light outputting unit) 11 and a light detector (light detecting unit) 12. The light source 11 outputs rays of measurement light L1 which are input to a predetermined light inputting position on the surface of skin 51 of the living body 50 and have predetermined wavelength components ($\lambda_1$, $\lambda_2$, and $\lambda_3$), respectively. This measurement light L1 is propagated inside the living body 50 and is output from the surface of the skin 51 of the living body 50. The light detector 12 detects the measurement light L1 output from a predetermined light detecting position on the surface of the skin 51 of the living body 50 and generates a detection signal in accordance with the intensity of the detected measurement light L1. The blood glucose measurement device 1 calculates the $O_2Hb$ concentration and the HHb concentration based on the detection signal output from the light detector 12, in consideration of the influence of absorption, scattering, or the like of the measurement light L1 due to $O_2Hb$ and HHb. For example, the predetermined wavelength components are included within a range of a red wavelength region of visible light to a near-infrared region (670 nm to 2,500 nm). As an example, $\lambda_1$, $\lambda_2$, and $\lambda_3$ are 735 nm, 810 nm, and 850 nm, respectively. Here, the measurement light L1 need only include these wavelength components, and the measurement light L1 itself may be white light.

The part (a) of FIG. 3 is a plan view illustrating a configuration of the light measurement instrument 10. In addition, the part (b) of FIG. 3 is a sectional side view cut along line III-III in the part (a) of FIG. 3. The light source 11 and the light detector 12 are disposed with an interval of 5 cm therebetween, for example, and is integrated with a holder 13 made of soft black silicone rubber. This interval may be within a range of 3 cm to 4 cm.

For example, the light source 11 is a light source, such as a light emitting diode (LED), a laser diode (LD), or a super-luminescent diode (SLD). The measurement light L1 output from the light source 11 is input to the surface of the skin 51 of the living body 50 in a substantially perpendicular manner. The light detector 12 has N (N is an integer equal to or larger than 1) light detecting elements 16 and a preamplifier 17. The light detector 12 detects measurement light propagated inside the living body 50 and generates a detection signal in accordance with the intensity of the measurement light. For example, each of the light detecting elements 16 is a point sensor such as a photodiode or an avalanche photodiode, or an image sensor such as a CCD image sensor or a CMOS image sensor, having light sensitivity with respect to a wavelength region including the center wavelength of the measurement light output from the light source. For example, the light detector 12 has N light detecting elements 16 which are arranged in an array shape in a distance direction from the light source 11. The preamplifier 17 integrates photocurrents output from the light detecting elements 16 and amplifies the integrated photocurrents. The light detector 12 sensitively detects a faint signal via the preamplifier 17, generates a detection signal, and transmits this signal to the main body unit 30 through a cable 18. For example, the light measurement instrument 10 may pinch the living body 50 such as a finger or an ear or may be fixed to the living body 50 such as the head with a stretchable band.

FIG. 4 is a block diagram illustrating an example of a configuration of the blood glucose measurement device 1. The main body unit 30 is a computer having a CPU 24, a display (display unit) 25, a ROM 26, a RAM 27, a data bus 28, a controller 29, and an input device (input unit) 31. The controller 29 includes a light source control unit 21, a sample and hold circuit 22, and an A/D converter circuit 23. The controller 29 controls an optical output of the light measurement instrument 10. For example, the controller 29 controls the output interval of measurement light and the intensity of measurement light.

The light source control unit 21 is electrically connected to the light source 11 of the light measurement instrument 10. The light source control unit 21 is electrically connected to the data bus 28 and receives an instruction signal for instructing driving of the light source 11 from the CPU 24 which is also electrically connected to the data bus 28 in the same manner. An instruction signal includes information such as an optical intensity and a wavelength (for example, a wavelength of any of the wavelengths $\lambda_1$, $\lambda_2$, and $\lambda_3$) of measurement light output from the light source 11. The light source control unit 21 drives the light source 11 based on an instruction signal received from the CPU 24. The light source control unit 21 outputs a drive signal to the light measurement instrument 10 through the cable 18.

A detection signal transmitted from the light measurement instrument 10 through the cable 18 is input and retained in the sample and hold circuit 22 and the A/D converter circuit 23 and is converted into a digital signal, thereby being output to the CPU 24. The sample and hold circuit 22 is electrically connected to the data bus 28 and receives a sample signal indicating a timing of retaining the detection signal from the CPU 24 via the data bus 28. When a sample signal is received, the sample and hold circuit 22 retains N detection signals input from the light measurement instrument 10. The sample and hold circuit 22 is electrically connected to the A/D converter circuit 23 and outputs each of N retained detection signals to the A/D converter circuit 23.

The CPU 24 is a computation unit in the present embodiment. The CPU 24 computes the $O_2Hb$ concentration and the HHb concentration inside the living body 50, based on a detection signal received from the A/D converter circuit 23. The CPU 24 computes the time lag between a time change in the $O_2Hb$ concentration and a time change in the HHb concentration which have been calculated, and computes the blood glucose level based on the time lag, thereby sending the blood glucose level to the display 25 via the data bus 28. A method of computing an $O_2Hb$ concentration and an HHb concentration based on a detection signal, a method of computing a time lag, and a method of computing a blood glucose level will be described below. The display 25 is electrically connected to the data bus 28 and displays results sent from the CPU 24 via the data bus 28. For example, the display 25 and the input device 31 may be constituted of a touch panel display.

Next, an operation of the blood glucose measurement device 1 will be described. Furthermore, the blood glucose calculation method according to the present embodiment will be described. For example, this blood glucose calculation method is suitably performed by the CPU 24 which reads and executes a program stored in a non-transitory storage medium such as the ROM 26. FIG. 5 is a flowchart illustrating the blood glucose calculation method according to the present embodiment. First, the light source control unit 21 sequentially outputs rays of measurement light having the wavelengths $\lambda_1$ to $\lambda_3$, based on an instruction signal from the CPU 24. The rays of measurement light are input to the inside of the living body 50 from the light inputting position (light inputting step, S11). The rays of measurement light input to the inside scatter inside the living body 50 and are propagated while being absorbed into measurement subject components, and a part of the rays of light reaches the light detecting position of the living body 50. The rays of measurement light which have reached the light detecting position are detected by N light detecting elements 16 (light detecting step, S12). Each of the light detecting elements 16 generates a photocurrent in accordance with the intensity of detected measurement light. The photocurrent is converted into a detection signal by the preamplifier 17. The detection signal is sent to the sample and hold circuit 22 of the main body unit 30 and is retained therein, thereby being converted into a digital signal by the A/D converter circuit 23.

Here, the part (a) of FIG. 6 is a view illustrating an input timing of the rays of measurement light having the wavelengths $\lambda_1$ to $\lambda_3$, and the part (b) of FIG. 6 is a view illustrating an output timing of a digital signal from the A/D converter circuit 23. As illustrated in the part (a) of FIG. 6 and the part (b) of FIG. 6, when a laser beam having the wavelength $\lambda_1$ is input, N digital signals $D_1(1)$ to $D_1(N)$ corresponding to N light detecting elements 16 are sequentially obtained. Subsequently, when measurement light having the wavelength $\lambda_2$ is input, N digital signals $D_2(1)$ to $D_2(N)$ corresponding to N light detecting elements 16 are sequentially obtained. In this manner, (3×N) digital signals $D_1(1)$ to $D_3(N)$ are output from the A/D converter circuit 23.

Subsequently, the CPU 24 computes the $O_2Hb$ concentration and the HHb concentration by using at least one digital signal of the digital signals $D_1(1)$ to $D_3(N)$ (first computation step, S13).

Here, the computation of the CPU 24 in Step S13 will be described in detail based on an example of the relative amount of temporal change in the $O_2Hb$ concentration ($\Delta O_2Hb$) and the relative amount of temporal change in the HHb concentration ($\Delta HHb$). When values of detection signals corresponding to the measurement light wavelengths $\lambda_1$ to $\lambda_3$ at a time $T_0$ at a certain light detecting position are $D_{\lambda 1}(T_0)$ to $D_{\lambda 3}(T_0)$, respectively, and when values thereof at a time $T_1$ are $D_{\lambda 1}(T_1)$ to $D_{\lambda 3}(T_1)$ similarly, the amounts of change in the intensity of detected light at the times $T_0$ to $T_1$ are expressed as in the following Expressions (1) to (3), respectively.

[Math. 1]
$$\Delta OD_1(T_1) = \log\left(\frac{D_{\lambda 1}(T_1)}{D_{\lambda 1}(T_0)}\right) \quad (1)$$

[Math. 2]
$$\Delta OD_2(T_1) = \log\left(\frac{D_{\lambda 2}(T_1)}{D_{\lambda 2}(T_0)}\right) \quad (2)$$

[Math. 3]
$$\Delta OD_3(T_1) = \log\left(\frac{D_{\lambda 3}(T_1)}{D_{\lambda 3}(T_0)}\right) \quad (3)$$

Here, in Expressions (1) to (3), $\Delta OD_1(T_1)$ indicates the amount of temporal change in the intensity of detected light having the wavelength $\lambda_1$, $\Delta OD_2(T_1)$ indicates the amount of change in the intensity of detected light having the wavelength $\lambda_2$, and $\Delta OD_3(T_1)$ indicates the amount of temporal change in the intensity of detected light having the wavelength $\lambda_3$. In addition, when the relative amounts of temporal change in the concentrations of $O_2Hb$ and HHb during a period of the time $T_0$ to the time $T_1$ are $\Delta O_2Hb(T_1)$ and $\Delta HHb(T_1)$, respectively, these can be obtained by the following Expression (4).

[Math. 4]
$$\begin{pmatrix} \Delta O_2Hb(T_1) \\ \Delta HHb(T_1) \end{pmatrix} = \begin{pmatrix} a_{11} & a_{12} & a_{13} \\ a_{21} & a_{22} & a_{23} \end{pmatrix} \begin{pmatrix} \Delta OD_1(T_1) \\ \Delta OD_2(T_1) \\ \Delta OD_3(T_1) \end{pmatrix} \quad (4)$$

Here, in Expression (4), coefficients $a_{11}$ to $a_{23}$ are constants obtained from light absorption coefficients of $O_2Hb$ and HHb with respect to rays of light having the wavelengths $\lambda_1$, $\lambda_2$, and $\lambda_3$. The CPU 24 performs the foregoing computation of one detection signal of those at N light detecting positions and calculates $\Delta O_2Hb$ and $\Delta HHb$. For example, the calculation cycle thereof is 16 milliseconds.

Subsequently, the CPU 24 performs time differentiation of the time-series data of each of $\Delta O_2Hb$ and $\Delta HHb$ once or more to obtain a differential value (first differential value) of $\Delta O_2Hb$ and a differential value (second differential value) of $\Delta HHb$ (first computation step, S14). The relative amounts of temporal change $\Delta O_2Hb$ and $\Delta HHb$ include undulation components due to breathing or physiological action inside the body. The undulation components are frequency components smaller than that in a frequency caused by spontaneous heartbeats. Accordingly, there is concern that the computation accuracy will be degraded. Therefore, in the present embodiment, correction of $\Delta O_2Hb$ and $\Delta HHb$ is performed to reduce (or eliminate) frequency components smaller than that in a frequency caused by spontaneous heartbeats. That is, the first differential value and the second differential value, in which small frequency components are reduced, are obtained by performing differentiation of $\Delta O_2Hb$ and $\Delta HHb$ once or performing differentiation thereof twice. Instead of such a method, frequency components smaller than that in a frequency of spontaneous heartbeats (for example, components of 0.5 Hz or lower) may be eliminated by performing filtering.

The part (a) of FIG. 7 is a graph showing the time-series data of actual measurement values of $\Delta O_2Hb$ and $\Delta HHb$. A graph G10 shows the time-series data of $\Delta O_2Hb$ (time change in the $O_2Hb$ concentration). A graph G11 shows the time-series data of $\Delta HHb$ (time change in the HHb concentration). The part (b) of FIG. 7 is a graph showing the data obtained by performing differentiation of the time-series data of the actual measurement values of $\Delta O_2Hb$ once and the data obtained by performing differentiation of the time-series data of the actual measurement values of $\Delta HHb$ once. A graph G12 shows the time-series data of the value obtained by performing differentiation of $\Delta O_2Hb$ once (time change in the value obtained by performing differentiation of the $O_2Hb$ concentration once). A graph G13 shows the time-series data of the value obtained by performing differentiation of $\Delta HHb$ once (time change in the value obtained by performing differentiation of the HHb concentration once). The part (c) of FIG. 7 is a graph showing the data obtained by performing differentiation of the time-series data of the actual measurement values of $\Delta O_2Hb$ twice and the data obtained by performing differentiation of the time-series data of the actual measurement values of $\Delta HHb$ twice. A graph G14 shows the time-series data of the values obtained by performing differentiation of $\Delta O_2Hb$ twice (time change in the values obtained by performing differentiation of the $O_2Hb$ concentration twice). A graph G15 shows the time-series data of the values obtained by performing differentiation of $\Delta HHb$ twice (time change in the values obtained by performing differentiation of the HHb concentration twice).

With reference to the part (a) of FIG. 7, in the graphs G10 and G11, the peak value and the bottom value repeatedly appearing in a cycle significantly fluctuate in each cycle. The peak value indicates the maximum value in a heartbeat cycle, and the bottom value indicates a starting point of heartbeats in a heartbeat cycle. This indicates that undulation components due to breathing or physiological action inside the body are included in $\Delta O_2Hb$ and $\Delta HHb$. In contrast, with reference to the part (b) of FIG. 7 and the part (c) of FIG. 7, in the graphs G12 to G15, fluctuations in each cycle of the peak value and the bottom value repeatedly appearing in a cycle are reduced. That is, undulation components (low-frequency components) of $\Delta O_2Hb$ and $\Delta HHb$ are relatively restrained. The method of correction (suppression of undulation components) performed with respect to $\Delta O_2Hb$ and $\Delta HHb$ is not limited to such a method. For example, processing of eliminating smaller frequency components than a predetermined frequency from $\Delta O_2Hb$ and $\Delta HHb$ may be performed.

With reference to FIG. 5 again, the blood glucose measurement device 1 according to the present embodiment performs operations as follows. That is, the CPU 24 calculates the time lag between the $O_2Hb$ concentration and the HHb concentration based on the $O_2Hb$ concentration and the HHb concentration calculated by the method described above (first computation step, S15). Next, based on this time lag, the CPU 24 calculates the blood glucose level (second computation step, S16). In the blood glucose calculation method and the blood glucose calculation program according to the present embodiment, the foregoing Steps S11 to S16 are repeatedly performed. Hereinafter, a method of calculating a time lag and a method of calculating a blood glucose level will be described in detail based on an example of the relative amount of temporal change in the $O_2Hb$ concentration ($\Delta O_2Hb$) and the relative amount of temporal change in the HHb concentration ($\Delta HHb$).

For example, the time lag between $\Delta O_2Hb$ and $\Delta HHb$ is suitably calculated by a first method, a second method, or a third method. First, the first method is a calculation method in which a feature point is extracted. In the first method, the CPU 24 obtains a first feature point repeatedly appearing in a cycle in $\Delta O_2Hb$ and a second feature point, corresponding to the first feature point, repeatedly appearing in a cycle in $\Delta HHb$. Then, the CPU 24 obtains the time lag based on the time difference between the first feature point and the second feature point. Alternatively, the CPU 24 obtains the first feature point repeatedly appearing in a cycle in the values obtained by performing differentiation of $\Delta O_2Hb$ M times (M is an integer equal to or larger than 1) and the second feature point, corresponding to the first feature point, repeatedly appearing in a cycle in the values obtained by performing differentiation of $\Delta HHb$ M times. Then, the CPU 24 obtains the time lag based on the time difference between the first feature point and the second feature point.

As an example, the part (a) of FIG. 8 is a graph for describing the method of calculating a time lag performed by extracting a feature point in the value obtained by performing differentiation of $\Delta O_2Hb$ and $\Delta HHb$ once. A graph G20 shows the value obtained by performing differentiation of $\Delta O_2Hb$ once. A graph G21 shows the value obtained by performing differentiation of $\Delta HHb$ once. For example, these graphs include several feature points, such as a peak point, a bottom point, and a notch point. The notch point is a point indicating a local depression in the time-series data. The CPU 24 extracts the feature point at a plurality of spots. For example, with reference to the part (a) of FIG. 8, peak points P1 to P3 and bottom points B1 to B3 repeatedly appearing in a cycle in $\Delta O_2Hb$, and peak points P4 to P6 and the bottom points B4 to B6 repeatedly appearing in a cycle in $\Delta HHb$ are extracted. The CPU 24 obtains time lags $\Delta t1$ to $\Delta t3$ between peak points and time lags $\Delta t4$ to $\Delta t6$ between bottom points, corresponding to each other. For example, the average value of these time lags $\Delta t1$ to $\Delta t6$ may be adopted as the time lag between $\Delta O_2Hb$ and $\Delta HHb$.

The second method is a calculation method performed with a value of an inner product. In the second method, the CPU 24 obtains the time lag based on the value of the inner product of a function of $\Delta O_2Hb$ and a function of $\Delta HHb$ during a predetermined period. Alternatively, the CPU 24 may obtain a time lag based on the value of the inner product of a function of the values obtained by performing differentiation of $\Delta O_2Hb$ M times and a function of the values obtained by performing differentiation of $\Delta HHb$ M times during a predetermined period. As an example, the part (b) of FIG. 8 is a graph for describing the method of calculating a time lag performed based on an inner product of functions of the value obtained by performing differentiation of $\Delta O_2Hb$ once and the value obtained by performing differentiation of $\Delta HHb$ once. Similar to vectors, the inner product can also be applied to the functions. When the function of $\Delta O_2Hb$ and the function of $\Delta HHb$ are standardized and the inner product is computed, the value of the inner product thereof becomes equivalent to the value of $\cos(\Delta\theta)$. The factor $\Delta\theta$ is a phase shift between $\Delta O_2Hb$ and $\Delta HHb$. The phase shift ($\Delta\theta$) can be obtained based on this relationship, and the time lag is calculated by the following Expression (5). Here, T is a heartbeat cycle.

[Math. 5]

$$\Delta t = \arccos\Delta\theta \times \frac{1}{2\pi} \times T \qquad (5)$$

The third method is a calculation method performed by comparing centroid positions to each other. In the third method, the CPU 24 obtains a centroid position in $\Delta O_2Hb$ (first centroid position) and obtains a centroid position in $\Delta HHb$ (second centroid position), thereby obtaining a time lag based on the time difference between these centroid positions, during a predetermined period. Alternatively, the CPU 24 may obtain a centroid position in the values obtained by performing differentiation of $\Delta O_2Hb$ M times (first centroid position) and may obtain a centroid position in the values obtained by performing differentiation of $\Delta HHb$ M times (second centroid position), thereby obtaining a time lag based on the time difference between these centroid positions, during a predetermined period. In the calculation method of comparing centroid positions, the centroid position is unlikely to fluctuate due to an influence of noise. Therefore, a time lag can be accurately obtained.

The part (c) of FIG. 8 is a graph for describing a method of calculating a time lag performed by extracting a centroid position based on the time-series data of the value obtained by performing differentiation of $\Delta O_2Hb$ and $\Delta HHb$ once. As illustrated in the part (c) of FIG. 8, the CPU 24 obtains a first centroid position $G_1$ and a second centroid position $G_2$ of $\Delta O_2Hb$ and $\Delta HHb$ during a predetermined period and calculates the time lag $\Delta t$ based on these centroid positions $G_1$ and $G_2$. For example, the time lag $\Delta t$ is obtained as a time difference between the centroid positions $G_1$ and $G_2$. For example, the predetermined period may be set based on the time lag between $\Delta O_2Hb$ and ABM calculated by either the first method or second method described above and cycles thereof.

Subsequently, the CPU 24 calculates the blood glucose level based on the time lag calculated by the first method, the second method, or the third method described above. The part (a) of FIG. 9 is a graph showing an example of the time-series data of the value obtained by performing differentiation of $\Delta O_2Hb$ and $\Delta HHb$ once when an examinee is in a hyperglycemia state. The part (b) of FIG. 9 is a graph showing an example of the time-series data of the value obtained by performing differentiation of $\Delta O_2Hb$ and $\Delta HHb$ once when an examinee is in a hypoglycemia state. In the part (a) of FIG. 9 and the part (b) of FIG. 9, graphs G30 and G32 show the time-series data of the value obtained by performing differentiation of $\Delta O_2Hb$ once. Graphs G31 and G33 show the time-series data of the value obtained by performing differentiation of $\Delta HHb$ once.

With reference to the part (a) of FIG. 9 and the part (b) of FIG. 9, the time lag of $\Delta HHb$ with respect to $\Delta O_2Hb$ is small when an examinee is in a hyperglycemia state and is large when an examinee is in a hypoglycemia state. That is, it is understood that there is a meaningful correlationship between a blood glucose level and a time lag. Moreover, from Examples (which will be described below), the inventor has found that a relationship between a blood glucose level and a time lag is expressed as the following mathematical expression. The factor G is a blood glucose level, and the factor $\Delta t$ is a time lag. A first coefficient $\alpha$ and a second coefficient $\beta$ are coefficients set in accordance with the maximum of glycometabolism ability and a measurement site.

[Math. 6]

$$G = \alpha \frac{1}{\Delta t} - \beta \quad (6)$$

The first coefficient $\alpha$ and the second coefficient $\beta$ are coefficients depending on the measurement site such as an ear lobe, a finger, or the forehead. In addition, the first coefficient $\alpha$ and the second coefficient $\beta$ also depends on glycometabolism ability. Therefore, the blood glucose level can be accurately obtained by setting the first coefficient $\alpha$ and the second coefficient $\beta$ for each measurement site in consideration of the maximum of glycometabolism ability of an examinee and using Expression (6).

The blood glucose measurement device, the blood glucose calculation method, and the blood glucose calculation program according to the present embodiment may further include the input device 31 that receives inputs of the first coefficient $\alpha$ and the second coefficient $\beta$ from outside (refer to FIG. 4). For example, when the values of the first coefficient $\alpha$ and the second coefficient $\beta$ are set through comparison between the blood glucose level obtained by a technique in the related art in a regular examination and a blood glucose level calculated by Expression (6), the values of the first coefficient $\alpha$ and the second coefficient $\beta$ may be input by using the input device 31 and may be saved in the ROM 26 serving as a storing unit (refer to FIG. 4). In addition, for example, when age and gender of an examinee, and the parameters of the blood glucose level at the time of a regular examination are statistically saved in the ROM 26, and when personal information of an examinee is input to the input device 31, an adequate first coefficient $\alpha$ and an adequate second coefficient $\beta$ may be selected.

The effects of the blood glucose measurement device 1, the blood glucose calculation method, and the blood glucose calculation program according to the present embodiment having the foregoing configuration will be described below. In the present embodiment, the blood glucose level is calculated based on the time lag between the parameter related to the $O_2Hb$ concentration (for example, the $O_2Hb$ concentration or the values obtained by performing differentiation of the $O_2Hb$ concentration M times) and the parameter related to the $HHb$ concentration (for example, the $HHb$ concentration or the values obtained by performing differentiation of the $HHb$ concentration M times). In the related art, it has been assumed that the temporal change in the $O_2Hb$ concentration and the temporal change in the $HHb$ concentration in accordance with spontaneous heartbeats are synchronized with each other. However, the inventor has found that a time lag sometimes occurs between the temporal change in the $O_2Hb$ concentration and the temporal change in the $HHb$ concentration, and the magnitude of the time lag depends on the glucose concentration in blood (blood glucose level). The magnitude of the time lag is within a range of 0.1 seconds to 0.2 seconds in a case of a healthy person, for example.

An absorption wavelength region of hemoglobin scarcely overlaps the absorption wavelength regions of components such as water, lipids, and proteins. Furthermore, the weight ratio of hemoglobin in blood is remarkably higher than the weight ratio of glucose. Therefore, the blood glucose level can be accurately measured by measuring the blood glucose level based on the time lag between the temporal change in the $O_2Hb$ concentration and the temporal change in the $HHb$ concentration. In addition, the amount of the time lag between the temporal change in the $O_2Hb$ concentration and the temporal change in the $HHb$ concentration is equivalent to the amount of the time lag between the temporal changes in the values obtained by performing differentiation of these M times. Therefore, similarly, the blood glucose level can also be accurately measured by measuring the blood glucose level based on the time lag between the temporal change in the values obtained by performing differentiation of the $O_2Hb$ concentration M times and the temporal change in the values obtained by performing differentiation of the $HHb$ concentration M times.

In addition, as in the present embodiment, each of the differential values of the $O_2Hb$ concentration and the $HHb$ concentration used in calculation of a time lag may be a value in which frequency components smaller than that in a frequency caused by spontaneous heartbeats are eliminated by performing time differentiation at least once or more with respect to the time-series data of the $O_2Hb$ concentration and the $HHb$ concentration. Accordingly, the influence of frequency components smaller than that in a frequency caused by spontaneous heartbeats applied to computation results can be restrained, so that the time lag can be more accurately obtained.

In addition, as in the present embodiment, the CPU 24 may obtain a time lag based on the time difference between the feature point repeatedly appearing in a cycle in the temporal change in the parameter related to the $O_2Hb$ concentration and the feature point repeatedly appearing in a cycle in the temporal change in the parameter related to the $HHb$ concentration. Accordingly, the time lag in parameters can be easily obtained.

In addition, as in the present embodiment, the CPU 24 may obtain a time lag between the temporal changes in the parameters thereof based on the value of the inner product of the function of the parameter related to the $O_2Hb$ concentration and the function of the parameter related to the HHb concentration obtained during a predetermined period. Accordingly, the time lag in parameters can be easily obtained.

In addition, as in the present embodiment, the CPU 24 may obtain a time lag between the temporal changes in the parameters thereof based on the time difference between the centroid position in the temporal change in the parameter related to the $O_2Hb$ concentration and the centroid position in the temporal change in the parameter related to the HHb concentration obtained during a predetermined period. Accordingly, the time lag in parameters can be easily obtained.

In addition, as in the present embodiment, the CPU 24 may obtain a blood glucose level based on the fact that the blood glucose level is in inverse proportion to the time lag between the temporal change in the $O_2Hb$ concentration and the temporal change in the $O_2Hb$ concentration. Accordingly, the blood glucose level can be accurately obtained. Particularly, the blood glucose level can be more accurately obtained when the CPU 24 obtains the blood glucose level by using Expression (6) described above.

EXAMPLES

FIG. 10 is a scatter diagram showing a correlationship between a blood glucose level of an examinee A obtained by using an invasive blood glucose meter and the time lag $\Delta t$ between $\Delta O_2Hb$ and $\Delta HHb$ measured in an ear lobe of the examinee A by using the blood glucose measurement device 1 according to the embodiment after the examinee A in a seated position has ingested a carbonated drink (Coca-Cola (registered trademark)). In FIG. 10, the vertical axis indicates the time lag $\Delta t$ (unit: second), and the horizontal axis indicates the blood glucose level (unit: mg/dl). The blood glucose level and the time lag $\Delta t$ were measured at a predetermined time interval during 11 days after the examinee A ingested a carbonated drink. Since the carbonated drink includes a large amount of glucose, when the carbonated drink was ingested, the blood glucose level of the examinee A increased. Accordingly, the correlationship between the blood glucose level and the time lag $\Delta t$ could be ascertained.

With reference to FIG. 10, it was possible to confirm that when the blood glucose level decreased, the time lag $\Delta t$ increased, and when the blood glucose level increased, the time lag $\Delta t$ decreased and the correlationship therebetween had approximately a linear shape. In other words, it was possible to confirm that there was a correlationship between the time lag $\Delta t$ measured by using the blood glucose measurement device 1 of the embodiment and the blood glucose level obtained by using an invasive blood glucose meter in substantially inverse proportion to each other. In all of the measurement points shown in FIG. 10, measurement was performed while the examinee A was under the same condition (ingesta, the measurement device, the measurement site, and the posture). Therefore, it was ascertained that measurement using the blood glucose measurement device 1 according to the embodiment had reproducibility.

The part (a) of FIG. 11 is a scatter diagram showing a correlationship between the blood glucose level of the examinee A obtained by using an invasive blood glucose meter and the time lag $\Delta t$ measured in an ear lobe of the examinee A by using the blood glucose measurement device 1 according to the embodiment after the examinee A in the supine position has ingested a carbonated drink. The part (b) of FIG. 11 is a scatter diagram showing a correlationship between the blood glucose level of an examinee B obtained by using an invasive blood glucose meter and the time lag $\Delta t$ measured in an ear lobe of the examinee B by using the blood glucose measurement device 1 of the embodiment after the examinee B in the supine position has ingested a pastry. The part (a) of FIG. 12 is a scatter diagram showing a correlationship between the blood glucose level of an examinee C obtained by using an invasive blood glucose meter and the time lag $\Delta t$ measured in an ear lobe of the examinee C by using the blood glucose measurement device 1 of the embodiment after the examinee C in the supine position has ingested a pastry. The part (b) of FIG. 12 is a view in which the scatter diagrams of the part (a) of FIG. 11, the part (b) of FIG. 11, and the part (a) of FIG. 12 are combined in one. In these diagrams, the horizontal axis indicates the time lag $\Delta t$ (unit: second), and the vertical axis indicates the blood glucose level (unit: mg/dl). Graphs G40 to G43 are power approximation curves of these scatter diagrams. Since a carbonated drink and a pastry are foods including a large amount of glucose, the blood glucose levels of the examinees A to C significantly rose after these were ingested.

With reference to the part (a) of FIG. 11, the part (b) of FIG. 11, the part (a) of FIG. 12, and the part (b) of FIG. 12, it was possible to confirm that there is a correlationship between the time lag $\Delta t$ measured by using the blood glucose measurement device 1 and the blood glucose level obtained by using an invasive blood glucose meter in substantially inverse proportion to each other, in the examinees A to C. Therefore, there was a reversely proportional correlationship between the time lag $\Delta t$ measured by using the blood glucose measurement device 1 and the blood glucose level obtained by using an invasive blood glucose meter, and it was indicated that the influence due to the difference between the examinees (individual difference) was small in this correlationship.

The part (a) of FIG. 13, the part (b) of FIG. 13, the part (a) of FIG. 14, and the part (b) of FIG. 14 are scatter diagrams when the horizontal axes of the part (a) of FIG. 11, the part (b) of FIG. 11, the part (a) of FIG. 12, and the part (b) of FIG. 12 are set to the reciprocal of the time lag ($1/\Delta t$, unit: Hz). Graphs G44 to G47 are power approximation curves of these scatter diagrams. In these diagrams, the vertical axis indicates the blood glucose level (unit: mg/dl). With reference to the part (a) of FIG. 13, the part (b) of FIG. 13, the part (a) of FIG. 14, and the part (b) of FIG. 14, it was possible to confirm that the blood glucose level measured by using an invasive blood glucose meter was substantially in proportional to the reciprocal of the time lag ($1/\Delta t$) measured by using the blood glucose measurement device 1.

From the measurement results of the present Example described above, the relationship between a blood glucose level (G) and the reciprocal of the time lag ($1/\Delta t$) is expressed as the following mathematical expression.

[Math. 7]

$$G = 30 \frac{1}{\Delta t} - 125 \quad (7)$$

In the present Example, the foregoing Expression (7) was introduced as a common relation expression with respect to the plurality of examinees A to C. As the reason for this, it was assumed that the examinees A to C was comparatively healthy and measurement was performed in the same measurement site (ear lobe). When the glycometabolism ability and the measurement site are different from each other, it is desirable that each of the coefficients in Expression (7), that is, the coefficients $\alpha$ and $\beta$ in Expression (6) be adjusted. Accordingly, the blood glucose level can be more accurately obtained. According to the experiments of the inventor, the coefficients $\alpha$ and $\beta$ were constant over a long period of time (half year) in measurement of the same person at the same site.

The part (a) to the part (c) of FIG. 15 are graphs showing time changes in the blood glucose levels of the examinees A to C measured by using an invasive blood glucose meter (graphs G53 to 55) and time changes in the reciprocal of the time lag (1/$\Delta$t) measured in an ear lobe of the examinee A by using the blood glucose measurement device 1 (graphs G50 to 52), in an overlapping manner and correspond to the part (a) of FIG. 11, the part (b) of FIG. 11, and the part (a) of FIG. 12, respectively. In these diagrams, the horizontal axis indicates the time (unit: minute), the vertical axis on the left indicates the blood glucose level (unit: mg/dl) obtained by using an invasive blood glucose meter, and the vertical axis on the right indicates the reciprocal of the time lag (1/$\Delta$t, unit: Hz) measured by using the blood glucose measurement device 1. With reference to the part (a) to the part (c) of FIG. 15, it was possible to confirm that the reciprocal of the time lag (1/$\Delta$t) measured by using the blood glucose measurement device 1 followed the blood glucose level obtained by using an invasive blood glucose meter without significantly depending on the individual difference.

In the part (a) to the part (c) of FIG. 15, a correlation coefficient $R^2$ between the reciprocal of the time lag (1/$\Delta$t) measured by using the blood glucose measurement device 1 and the blood glucose level obtained by using an invasive blood glucose meter was −0.74 in the part (a) of FIG. 15, was −0.93 in the part (b) of FIG. 15, and was −0.83 in the part (c) of FIG. 15, manifesting a close correlationship between all the cases. Therefore, it was possible to confirm that there was a close correlationship between the reciprocal of the time lag (1/$\Delta$t) measured by using the blood glucose measurement device 1 according to the embodiment and the blood glucose level obtained by using an invasive blood glucose meter. A method of calculating the correlation coefficient $R^2$ will be described below.

The part (a) of FIG. 16 is a graph showing a time change in the blood glucose level of the examinee A obtained by using an invasive blood glucose meter (graph G60) and a time change in the reciprocal of the time lag (1/$\Delta$t) measured in the front forehead of the examinee A by using the blood glucose measurement device 1 (graph G63) after the examinee A in a seated position has ingested jelly-like nutritional supplementary food (Weider In Jelly (registered trademark)), in an overlapping manner. The part (b) of FIG. 16 is a graph showing a time change in the blood glucose level of the examinee A obtained by using an invasive blood glucose meter (graph G61) and a time change in the reciprocal of the time lag (1/$\Delta$t) measured in the front forehead of the examinee A by using the blood glucose measurement device 1 (graph G64) after the examinee A in a seated position has ingested chicken meat (white meat), in an overlapping manner. In these diagrams, the horizontal axis indicates the elapsed time (unit: minute), the vertical axis on the left indicates the blood glucose level (unit: mg/dl) obtained by using an invasive blood glucose meter, and the vertical axis on the right indicates the reciprocal of the time lag (1/$\Delta$t, unit: Hz) measured by using the blood glucose measurement device 1. Since jelly-like nutritional supplementary food includes a large amount of glucose, the blood glucose level of the examinee A rose after the food was ingested and fell thereafter, as shown in the graph G60 in the part (a) of FIG. 16. In contrast, since white meat has proteins as a main component and includes little glucose, there was little change in the blood glucose level of the examinee A after white meat was ingested, as shown in the graph G61 in the part (b) of FIG. 16.

With reference to the part (a) of FIG. 16, the reciprocal of the time lag (1/$\Delta$t) measured by using the blood glucose measurement device 1 rose with the lapse of time and fell thereafter after the examinee A ingested jelly-like nutritional supplementary food. Accordingly, it was possible to confirm that the reciprocal of the time lag (1/$\Delta$t) favorably followed the time change in the blood glucose level obtained by using an invasive blood glucose meter. In addition, with reference to the part (b) of FIG. 16, it was possible to confirm that there is little change in the reciprocal of the time lag (1/$\Delta$t) measured by using the blood glucose measurement device 1 regardless of the lapse of time, after the examinee A ingested white meat. From these results, it was indicated that the reciprocal of the time lag (1/$\Delta$t) measured by using the blood glucose measurement device 1 according to the embodiment could suitably follow the time change in the blood glucose level.

In the part (a) of FIG. 16 and the part (b) of FIG. 16, the correlation coefficient $R^2$ between the reciprocal of the time lag (1/$\Delta$t) measured by using the blood glucose measurement device 1 and the blood glucose level obtained by using an invasive blood glucose meter was 0.82 in the part (a) of FIG. 16 and was 0.96 in the part (b) of FIG. 16. Generally, in the field of biological measurement, the correlation coefficient $R^2$ of 0.8 or larger is considered to have a close correlationship. Accordingly, these results can be considered to have a close correlationship. Therefore, it was possible to confirm that there was a close correlationship between the reciprocal of the time lag (1/$\Delta$t) measured by using the blood glucose measurement device 1 according to the embodiment and the blood glucose level obtained by using an invasive blood glucose meter.

Here, in a scatter diagram having x and y as variables, the correlation coefficient $R^2$ can be obtained by the following Expression (8).

[Math. 8]

$$R^2 = \frac{Sxy^2}{Sx \cdot Sy} \quad (8)$$

Here, Sx is the variance of x, Sy is the variance of y, and Sxy is the covariance of x and y. The variances Sx and Sy and the covariance Sxy are obtained by the following mathematical expressions (9) to (11), respectively. Here, $x_0$ and $y_0$ are the average values of x and y, respectively. In addition, n is a sample number.

[Math. 9]

$$Sx = \frac{1}{n}\sum_{i=1}^{n}(x_i - x_0)^2 \quad (9)$$

[Math. 10]
$$Sy = \frac{1}{n}\sum_{i=1}^{n}(y_i - y_0)^2 \quad (10)$$

[Math. 11]
$$Sxy = \frac{1}{n}\sum_{i=1}^{n}(x_i - x_0)(y_i - y_0) \quad (11)$$

For the sake of fast computation processing, the variances Sx and Sy and the covariance Sxy may be obtained by the method described below. That is, the variances Sx and Sy and the covariance Sxy can also be suitably obtained by the following mathematical expressions (12) to (14), respectively.

[Math. 12]
$$Sx = \sum_{i=1}^{n}(x_i^2 - nx_0^2) \quad (12)$$

[Math. 13]
$$Sy = \sum_{i=1}^{n}(y_i^2 - ny_0^2) \quad (13)$$

[Math. 14]
$$Sxy = \sum_{i=1}^{n}(x_i y_i - nx_0 y_0) \quad (14)$$

Therefore, for example, the variances Sx and Sy, the covariance Sxy, and the average values $x_0$ and $y_0$ is favorably obtained while having the time-series data of $\Delta O_2 Hb$ set to $x_1$ to $x_n$ and the time-series data of $\Delta HHb$ set to $y_1$ to $y_n$, obtained during a certain period of time (for example, for 5 seconds). The correlation coefficient $R^2$ can be obtained by substituting these in the foregoing mathematical expression (8).

The blood glucose measurement device, the blood glucose calculation method, and the blood glucose calculation program are not limited to the embodiment and Examples described above, and various other modifications can be made. For example, the blood glucose measurement device 1, the blood glucose calculation method, and the blood glucose calculation program according to the embodiments described above presents an examinee with the blood glucose level calculated based on the time lag between $\Delta O_2 Hb$ and $\Delta HHb$. However, the blood glucose measurement device, the blood glucose calculation method, and the blood glucose calculation program may be applied as a diabetes diagnostic device, a diabetes diagnostic method, and a diabetes diagnostic program presenting an examinee with a fact whether or not he/she is diabetic, using a calculated blood glucose level as a clue to determination.

The inventor presumes the reversely proportional correlationship between the time lag $\Delta t$ and the blood glucose level described above as follows. There are oxygen metabolism and a glycolysis system in metabolism of a living body. In the process of converting glucose in the glycolysis system into energy, substances called 2,3-BPG are generated. The substance 2,3-BPG has characteristics of separating oxygen from hemoglobin. Consequently, oxygenated hemoglobin is converted into deoxygenated hemoglobin due to 2,3-BPG. Since the substance 2,3-BPG increases when the blood glucose level rises, 2,3-BPG promotes deoxygenation of hemoglobin. Therefore, when the blood glucose level rises, a delay of the time change in the deoxygenated hemoglobin concentration with respect to the time change in the oxygenated hemoglobin concentration is decreased. That is, a reversely proportional correlationship is established between the time lag $\Delta t$ and the blood glucose level.

In addition, in the example of the foregoing embodiment, the computation unit (CPU 24) is built in the main body unit 30 such as a smart device. However, for example, the computation unit may be provided separately from the main body unit, such as a cloud server or a personal computer. In such a case, the computation unit may be connected to the main body unit via a network such as radio or the internet. In addition, in the foregoing embodiment, one computation unit performs calculation of $\Delta O_2 Hb$ and $\Delta HHb$ and calculation of the time lag therebetween. However, a part calculating $\Delta O_2 Hb$ and $\Delta HHb$ and a part calculating time lags therebetween may be provided separately from each other in the computation unit.

In addition, in the foregoing embodiment, a modified Beer-Lambert method (MBL method) is adopted as a method of calculating $\Delta O_2 Hb$ and $\Delta HHb$. However, other methods for near-infrared spectroscopy such as space-resolved spectroscopy (SRS method) may be used. In addition, the absolute value of the $O_2 Hb$ concentration and the absolute value of the HHb concentration can be obtained by using near-infrared spectroscopy such as time-resolved spectroscopy (TRS method) or phase modulation spectroscopy (PMS method).

In the related art, it has been assumed that a temporal change in the oxygenated hemoglobin concentration and a temporal change in the deoxygenated hemoglobin concentration in accordance with spontaneous heartbeats are synchronized with each other. However, the inventor has found that a time lag sometimes occurs between these temporal changes. Moreover, the inventor has found that the magnitude of the time lag depends on the glucose concentration in blood (blood glucose level). The absorption wavelength region of hemoglobin scarcely overlaps the absorption wavelength regions of components such as water, lipids, and proteins. Furthermore, the weight ratio of hemoglobin in blood is remarkably higher than the weight ratio of glucose. Therefore, as in the blood glucose measurement device, the blood glucose calculation method, and the blood glucose calculation program, the blood glucose level can be accurately measured (or calculated) by measuring the blood glucose level based on the time lag between the temporal change in the first parameter related to the oxygenated hemoglobin concentration and the temporal change in the second parameter related to the deoxygenated hemoglobin concentration.

In the embodiment, the first parameter may be the relative amount of temporal change or the absolute value of the oxygenated hemoglobin concentration, and the second parameter may be the relative amount of temporal change or the absolute value of the deoxygenated hemoglobin concentration. The blood glucose level can be accurately measured (calculated) by using a relative hemoglobin concentration or an absolute hemoglobin concentration as a parameter for obtaining a time lag.

In addition, the first parameter may be the first differential value obtained by performing time differentiation of the oxygenated hemoglobin concentration at least once, and the second parameter may be the second differential value obtained by performing time differentiation of the deoxygenated hemoglobin concentration at least once. The amount of the time lag between the temporal changes in the oxygenated hemoglobin concentration and the deoxygenated hemoglobin concentration may be equivalent to the amount of the time lag between the differential values of these temporal changes. Therefore, when the time lag is obtained by using a time change in the first differential value and a time change in the second differential value, the influence of frequency components smaller than that in a frequency caused by spontaneous heartbeats applied to computation results can be restrained, so that the time lag can be more accurately obtained.

In addition, the computation unit or the first computation step may obtain a time lag based on the time difference between the first feature point and the second feature point by obtaining the first feature point repeatedly appearing in a cycle in the temporal change in the first parameter and the second feature point, corresponding to the first feature point, repeatedly appearing in a cycle in the temporal change in the second parameter. Accordingly, the time lag can be easily obtained.

In addition, the computation unit or the first computation step may obtain a time lag based on the value of the inner product by obtaining the value of the inner product of the function of the first parameter and the function of the second parameter during a predetermined period. For example, when the function of the first parameter and the function of the second parameter are standardized and the inner product is obtained, the value thereof becomes equivalent to the value of $\cos(\Delta\theta)$. The time lag can be easily obtained based on the phase shift ($\Delta\theta$) calculated from this relationship.

In addition, the computation unit or the first computation step may obtain a time lag based on the time difference between the first centroid position and the second centroid position by obtaining the first centroid position in the temporal change in the first parameter and obtaining the second centroid position in the temporal change in the second parameter during a predetermined period. Accordingly, the time lag can be easily obtained.

In addition, the computation unit or the second computation step may obtain data related to the blood glucose level based on the fact that the blood glucose level is in inverse proportion to the time lag. The inventor has found that a reversely proportional correlationship is established between the blood glucose level and the time lag. Therefore, the blood glucose level can be accurately obtained based on this relationship.

In addition, the blood glucose measurement device described above may be characterized in that the computation unit or the second computation step obtains data related to the blood glucose level by using the following expression.

[Math. 15]

$$G = \alpha \frac{1}{\Delta t} - \beta \quad (15)$$

Here, the factor G is a blood glucose level, the factor $\Delta t$ is a time lag, the factor $\alpha$ is the first coefficient set in accordance with the maximum of glycometabolism ability and the measurement site, and the factor $\beta$ is the second coefficient set in accordance with the maximum of glycometabolism ability and the measurement site. The inventor has found that there is a correlationship which is expressed by the foregoing Expression and is established between the blood glucose level and the time lag. Since the first coefficient $\alpha$ and the second coefficient $\beta$ are set in accordance with the maximum of glycometabolism ability of an examinee, the blood glucose level is obtained in consideration of the maximum of glycometabolism ability of an examinee. In addition, since the first coefficient $\alpha$ and the second coefficient $\beta$ depend on the measurement site, the blood glucose level is obtained in consideration of the difference in measurement sites of an examinee. Accordingly, the blood glucose level can be more accurately obtained.

In addition, in the computation unit or the second computation step, the first coefficient and the second coefficient may be input from outside, and the computation unit may obtain the data related to the blood glucose level by using the first coefficient and the second coefficient input from outside. For example, the first coefficient and the second coefficient are adequately set in accordance with the maximum of glycometabolism ability by comparing the blood glucose level obtained by a technique in the related art a regular examination and the blood glucose level calculated by the foregoing device. Therefore, it is possible to suitably obtain a more accurate blood glucose level in accordance with the glycometabolism ability of a testee based on the first coefficient and the second coefficient input from outside.

In addition, the blood glucose calculation method of the embodiment may further include a light inputting step of inputting measurement light to a living body, and a light detecting step of detecting measurement light propagated inside the living body and generating a detection signal in accordance with the intensity of the measurement light.

INDUSTRIAL APPLICABILITY

Embodiments can be utilized as a blood glucose measurement device, a blood glucose calculation method, and a blood glucose calculation program.

REFERENCE SIGNS LIST

1 Blood glucose measurement device
10 Light measurement instrument
11 Light source (light outputting unit)
12 Light detector (light detecting unit)
13 Holder
16 Light detecting element
17 Preamplifier
18 Cable
21 Light source control unit
22 Sample and hold circuit
23 A/D converter circuit
24 CPU
25 Display (display unit)
26 ROM
27 RAM
28 Data bus
29 Controller
30 Main body unit
50 Living body

The invention claimed is:
1. A blood glucose measurement device for obtaining data related to a blood glucose level of a living body, the device comprising:
a light outputting device configured to output measurement light to be input to the living body;

a light detecting device configured to detect the measurement light propagated inside the living body and generate a detection signal in accordance with an intensity of the measurement light; and a computation device configured to obtain a time lag between a temporal change in a first parameter related to an oxygenated hemoglobin concentration and a temporal change in a second parameter related to a deoxygenated hemoglobin concentration based on the detection signal, and obtain the data related to the blood glucose level based on the time lag, wherein the first parameter is a first differential value obtained by performing time differentiation of the oxygenated hemoglobin concentration at least once, and the second parameter is a second differential value obtained by performing time differentiation of the deoxygenated hemoglobin concentration at least once.

2. The blood glucose measurement device according to claim 1, wherein the computation device obtains a first feature point repeatedly appearing in a cycle in the temporal change in the first parameter and a second feature point repeatedly appearing in a cycle in the temporal change in the second parameter and corresponding to the first feature point, and obtains the time lag based on a time difference between the first feature point and the second feature point.

3. The blood glucose measurement device according to claim 1, wherein the computation device obtains a value of an inner product of a function of the first parameter and a function of the second parameter during a predetermined period, and obtains the time lag based on the value of the inner product.

4. The blood glucose measurement device according to claim 1, wherein the computation device obtains a first centroid position in the temporal change in the first parameter during a predetermined period, obtains a second centroid position in the temporal change in the second parameter during the predetermined period, and obtains the time lag based on a time difference between the first centroid position and the second centroid position.

5. The blood glucose measurement device according to claim 1, wherein the computation device obtains the data related to the blood glucose level based on a fact that the blood glucose level is in inverse proportion to the time lag.

6. The blood glucose measurement device according to claim 5, wherein the computation device obtains the blood glucose level by using the following expression,

[Math. 1]

$$G = \alpha \frac{1}{\Delta t} - \beta$$

where, G indicates the blood glucose level, $\Delta t$ indicates the time lag, $\alpha$ indicates a first coefficient set in accordance with a maximum of glycometabolism ability and a measurement site, and $\beta$ indicates a second coefficient set in accordance with the maximum of glycometabolism ability and the measurement site.

7. The blood glucose measurement device according to claim 6, wherein the first coefficient and the second coefficient are input from outside, and wherein the computation device obtains the data related to the blood glucose level by using the first coefficient and the second coefficient input from outside.

8. A blood glucose calculation method for calculating data related to a blood glucose level of a living body, the method comprising:

receiving, by at least one hardware processor, a detection signal in accordance with an intensity of a measurement light propagated inside the living body;

obtaining, by the at least one hardware processor, a time lag between a temporal change in a first parameter related to an oxygenated hemoglobin concentration and a temporal change in a second parameter related to a deoxygenated hemoglobin concentration in the living body; and obtaining, by the at least one hardware processor, the data related to the blood glucose level based on the time lag, wherein the first parameter is a first differential value obtained by performing time differentiation of the oxygenated hemoglobin concentration at least once, and the second parameter is a second differential value obtained by performing time differentiation of the deoxygenated hemoglobin concentration at least once.

9. The blood glucose calculation method according to claim 8, further comprising:

inputting measurement light to the living body;

detecting, by the at least one hardware processor, the measurement light propagated inside the living body; and generating, by the at least one hardware processor, the detection signal in accordance with the intensity of the measurement light.

10. A non-transitory storage medium storing a blood glucose calculation program for calculating data related to a blood glucose level of a living body, the program causing a computer having at least one hardware processor to execute:

receiving, by the at least one hardware processor, a detection signal in accordance with an intensity of a measurement light propagated inside the living body;

obtaining, by the at least one hardware processor, a time lag between a temporal change in a first parameter related to an oxygenated hemoglobin concentration and a temporal change in a second parameter related to a deoxygenated hemoglobin concentration in the living body, and obtaining, by the at least one hardware processor, the data related to the blood glucose level based on the time lag, wherein the first parameter is a first differential value obtained by performing time differentiation of the oxygenated hemoglobin concentration at least once, and the second parameter is a second differential value obtained by performing time differentiation of the deoxygenated hemoglobin concentration at least once.

11. A blood glucose measurement device for obtaining data related to a blood glucose level of a living body, the device comprising:

a light outputting device configured to output measurement light to be input to the living body;

a light detecting device configured to detect the measurement light propagated inside the living body and generate a detection signal in accordance with an intensity of the measurement light; and a computation device configured to obtain a time lag between a temporal change in a first parameter related to an oxygenated hemoglobin concentration and a temporal change in a second parameter related to a deoxygenated hemoglobin concentration based on the detection signal, and obtain the data related to the blood glucose level based on the time lag, wherein the computation device obtains a first feature point repeatedly appearing in a cycle in the temporal change in the first parameter and a second feature point repeatedly appearing in a cycle in the temporal change in the second parameter and corresponding to the first feature point, and obtains the time lag based on a time difference between the first feature point and the second feature point.

12. A blood glucose measurement device for obtaining data related to a blood glucose level of a living body, the device comprising:

a light outputting device configured to output measurement light to be input to the living body;

a light detecting device configured to detect the measurement light propagated inside the living body and generate a detection signal in accordance with an intensity of the measurement light; and a computation device configured to obtain a time lag between a temporal change in a first parameter related to an oxygenated hemoglobin concentration and a temporal change in a second parameter related to a deoxygenated hemoglobin concentration based on the detection signal, and obtain the data related to the blood glucose level based on the time lag, wherein the computation device obtains a value of an inner product of a function of the first parameter and a function of the second parameter during a predetermined period, and obtains the time lag based on the value of the inner product.

13. A blood glucose measurement device for obtaining data related to a blood glucose level of a living body, the device comprising:

a light outputting device configured to output measurement light to be input to the living body;

a light detecting device configured to detect the measurement light propagated inside the living body and generate a detection signal in accordance with an intensity of the measurement light; and a computation device configured to obtain a time lag between a temporal change in a first parameter related to an oxygenated hemoglobin concentration and a temporal change in a second parameter related to a deoxygenated hemoglobin concentration based on the detection signal, and obtain the data related to the blood glucose level based on the time lag, wherein the computation device obtains a first centroid position in the temporal change in the first parameter during a predetermined period, obtains a second centroid position in the temporal change in the second parameter during the predetermined period, and obtains the time lag based on a time difference between the first centroid position and the second centroid position.

14. A blood glucose measurement device for obtaining data related to a blood glucose level of a living body, the device comprising:

a light outputting device configured to output measurement light to be input to the living body;

a light detecting device configured to detect the measurement light propagated inside the living body and generate a detection signal in accordance with an intensity of the measurement light; and a computation device configured to obtain a time lag between a temporal change in a first parameter related to an oxygenated hemoglobin concentration and a temporal change in a second parameter related to a deoxygenated hemoglobin concentration based on the detection signal, and obtain the data related to the blood glucose level based on the time lag, wherein the computation device obtains the data related to the blood glucose level based on a fact that the blood glucose level is in inverse proportion to the time lag.

15. A blood glucose calculation method for calculating data related to a blood glucose level of a living body, the method comprising:

receiving, by at least one hardware processor, a detection signal in accordance with an intensity of a measurement light propagated inside the living body;

obtaining, by the at least one hardware processor, a first feature point repeatedly appearing in a cycle in a temporal change in a first parameter related to an oxygenated hemoglobin concentration and a second feature point repeatedly appearing in a cycle in a temporal change in a second parameter related to a deoxygenated hemoglobin concentration in the living body and corresponding to the first feature point;

obtaining, by the at least one hardware processor, a time lag between the temporal change in the first parameter and the temporal change in a second parameter, wherein the time lag based on a time difference between the first feature point and the second feature point; and obtaining, by the at least one hardware processor, the data related to the blood glucose level based on the time lag.

16. A blood glucose calculation method for calculating data related to a blood glucose level of a living body, the method comprising:

receiving, by at least one hardware processor, a detection signal in accordance with an intensity of a measurement light propagated inside the living body;

obtaining, by the at least one hardware processor, a value of an inner product of a function of a first parameter related to an oxygenated hemoglobin concentration and a function of a second parameter related to a deoxygenated hemoglobin concentration in the living body during a predetermined period;

obtaining, by the at least one hardware processor, a time lag between a temporal change in the first parameter and a temporal change in the second parameter, wherein the time lag based on the value of the inner product; and obtaining, by the at least one hardware processor, the data related to the blood glucose level based on the time lag.

17. A blood glucose calculation method for calculating data related to a blood glucose level of a living body, the method comprising:

receiving, by at least one hardware processor, a detection signal in accordance with an intensity of a measurement light propagated inside the living body;

obtaining, by the at least one hardware processor, a time lag between a temporal change in a first parameter related to an oxygenated hemoglobin concentration and a temporal change in a second parameter related to a deoxygenated hemoglobin concentration in the living body;

obtaining, by the at least one hardware processor, a first centroid position in the temporal change in the first parameter during a predetermined period;

obtaining, by the at least one hardware processor, a second centroid position in the temporal change in the second parameter during the predetermined period, wherein the time lag based on a time difference between the first centroid position and the second centroid position; and obtaining, by the at least one hardware processor, the data related to the blood glucose level based on the time lag.

18. A blood glucose calculation method for calculating data related to a blood glucose level of a living body, the method comprising:

receiving, by at least one hardware processor, a detection signal in accordance with an intensity of a measurement light propagated inside the living body;

obtaining, by the at least one hardware processor, a time lag between a temporal change in a first parameter related to an oxygenated hemoglobin concentration and a temporal change in a second parameter related to a deoxygenated hemoglobin concentration in the living body; and obtaining, by the at least one hardware processor, the data related to the blood glucose level based on the time lag and a fact that the blood glucose level is in inverse proportion to the time lag.

19. A non-transitory storage medium storing a blood glucose calculation program for calculating data related to a blood glucose level of a living body, the program causing a computer having at least one hardware processor to execute:

receiving, by the at least one hardware processor, a detection signal in accordance with an intensity of a measurement light propagated inside the living body;

obtaining, by the at least one hardware processor, a first feature point repeatedly appearing in a cycle in a temporal change in a first parameter related to an oxygenated hemoglobin concentration and a second feature point repeatedly appearing in a cycle in a temporal change in a second parameter related to a deoxygenated hemoglobin concentration in the living body and corresponding to the first feature point;

obtaining, by the at least one hardware processor, a time lag between the temporal change in the first parameter and the temporal change in a second parameter, wherein the time lag based on a time difference between the first feature point and the second feature point; and obtaining, by the at least one hardware processor, the data related to the blood glucose level based on the time lag.

20. A non-transitory storage medium storing a blood glucose calculation program for calculating data related to a blood glucose level of a living body, the program causing a computer having at least one hardware processor to execute:

receiving, by the at least one hardware processor, a detection signal in accordance with an intensity of a measurement light propagated inside the living body;

obtaining, by the at least one hardware processor, a value of an inner product of a function of a first parameter related to an oxygenated hemoglobin concentration and a function of a second parameter related to a deoxygenated hemoglobin concentration in the living body during a predetermined period;

obtaining, by the at least one hardware processor, a time lag between a temporal change in the first parameter and a temporal change in the second parameter, wherein the time lag based on the value of the inner product; and obtaining, by the at least one hardware processor, the data related to the blood glucose level based on the time lag.

21. A non-transitory storage medium storing a blood glucose calculation program for calculating data related to a blood glucose level of a living body, the program causing a computer having at least one hardware processor to execute:

receiving, by the at least one hardware processor, a detection signal in accordance with an intensity of a measurement light propagated inside the living body;

obtaining, by the at least one hardware processor, a time lag between a temporal change in a first parameter related to an oxygenated hemoglobin concentration and a temporal change in a second parameter related to a deoxygenated hemoglobin concentration in the living body;

obtaining, by the at least one hardware processor, a first centroid position in the temporal change in the first parameter during a predetermined period;

obtaining, by the at least one hardware processor, a second centroid position in the temporal change in the second parameter during the predetermined period, wherein the time lag based on a time difference between the first centroid position and the second centroid position; and obtaining, by the at least one hardware processor, the data related to the blood glucose level based on the time lag.

22. A non-transitory storage medium storing a blood glucose calculation program for calculating data related to a blood glucose level of a living body, the program causing a computer having at least one hardware processor to execute:

receiving, by the at least one hardware processor, a detection signal in accordance with an intensity of a measurement light propagated inside the living body;

obtaining, by the at least one hardware processor, a time lag between a temporal change in a first parameter related to an oxygenated hemoglobin concentration and a temporal change in a second parameter related to a deoxygenated hemoglobin concentration in the living body; and obtaining, by the at least one hardware processor, the data related to the blood glucose level based on the time lag and a fact that the blood glucose level is in inverse proportion to the time lag.

* * * * *